US008598229B2

(12) United States Patent
Reddell et al.

(10) Patent No.: US 8,598,229 B2
(45) Date of Patent: Dec. 3, 2013

(54) TIGLIEN-3-ONE DERIVATIVES

(75) Inventors: Paul Warren Reddell, Yungaburra (AU); Victoria Anne Gordon, Yungaburra (AU)

(73) Assignee: QBiotics Limited, Yungaburra, Queensland (AU)

( * ) Notice: Subject to any disclaimer, the term of this patent is extended or adjusted under 35 U.S.C. 154(b) by 1003 days.

(21) Appl. No.: 12/158,461

(22) PCT Filed: Dec. 22, 2006

(86) PCT No.: PCT/AU2006/002001

§ 371 (c)(1),
(2), (4) Date: Nov. 17, 2008

(87) PCT Pub. No.: WO2007/070985

PCT Pub. Date: Jun. 28, 2007

(65) Prior Publication Data

US 2009/0182042 A1 Jul. 16, 2009

(30) Foreign Application Priority Data

Dec. 23, 2005 (AU) ................................ 2005907278

(51) Int. Cl.

*A61K 31/343* (2006.01)
*A01N 43/20* (2006.01)
*A01N 43/90* (2006.01)
*A01N 45/00* (2006.01)
*C07D 303/00* (2006.01)

(52) U.S. Cl.

USPC ............................ 514/475; 549/543; 549/545

(58) Field of Classification Search

USPC .................................. 549/543, 545; 514/475

See application file for complete search history.

(56) References Cited

PUBLICATIONS

Challacombe et al., "Neutrophils Are a Key Component of the Antitumor Efficacy of Topical Chemotherapy with Ingenol-3-Angelate," The Journal of Immunology 177: 8123-8132, 2006.
Cozzi et al., "Induction of Senescence in Diterpene Ester-Treated Melanoma Cells via Protein Kinase C-Dependent Hyperactivation of the Mitogen-Activated Protein Kinase Pathway," Cancer Res 66(20): 10083-91, 2006.
Hanipson et al., "PEP005, a selective small-molecule activator of protein kinase C. has potent antileukemic activity mediated via the delta Isoform of PKC," Blood 106(4): 1362-1368, 2005.
CA Abstract No. 69:10570, 1968.
CA Abstract No. 70:47622, 1968.
CA Abstract No. 88:37991, 1977.
CA Abstract No. 89:3208, 1978.
CA Abstract No. 89:192165, 1978.
CA Abstract No. 92:141462, 1979.
CA Abstract No. 93:232311, 1980.
CA Abstract No. 97:176609, 1982.
CA Abstract No. 101:147806, 1984.
CA Abstract No. 115:273076, 1991.
Brynes et al., "Plasminogen Activator Induction and Platelet Aggregation by Phorbol and Some of Its Derivatives: Correlation with Skin Irritancy and Tumor-promoting Activity," J Cancer Res Clin Oncol 97(3): 257-266, 1980.
Hafez et al., "Active Principles of the Thyrmelaeaceae, III. Skin Irritant and Cocarcinogenic Factors from Pimelea simplex," J Med Plant Res, Planta Medica 49(1): 3-8, 1983.
Tyler et al., "Synthesis and Structure—Activity Studies of Potential Antitumour Agents Derived from Esters of Phorbol," Aust J Chem 40(1): 193-200, 1987.

*Primary Examiner* — Taylor Victor Oh
(74) *Attorney, Agent, or Firm* — Seed IP Law Group PLLC

(57) ABSTRACT

The present invention relates to tiglien-3-one compounds and their use in methods of treating or preventing protozoal infections, bacterial infections, parasitic infections and cell proliferative disorders. The tiglien-3-one compounds are also used in methods of controlling pests in humans, animals, plants and the environment.

13 Claims, 7 Drawing Sheets

TIGLIEN-3-ONE DERIVATIVES

FIELD OF THE INVENTION

This invention relates to bioactive molecules. More particularly, this invention relates to tiglien-3-one derivatives of potential therapeutic benefit and/or of use as a pharmaceutical and as an agrochemical.

BACKGROUND OF THE INVENTION

Bio-discovery is a growing field, which investigates and screens for bioactive natural products from natural environments, including plants, microorganisms, coral and other marine life. In the search for bioactive natural products, biological material is screened for molecules having properties that may be of therapeutic benefit for potential use in a range of treatments, for example treatments for cancer, antiprotozoal treatments, antiparasitic treatments, antibiotic treatments and anti-inflammatory treatments, or for pesticidal activity.

SUMMARY OF THE INVENTION

The present invention arises from the discovery of new tiglien-3-one derivatives which have potentially new therapeutic uses as cytotoxic agents, antiprotozoal agents, antiparasitic agents and antibiotic agents or potential as pesticidal agents for agricultural use.

One aspect of the invention provides compounds of the formula I

I

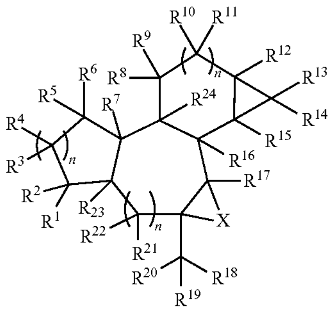

wherein:

X is selected from —S—, —O—, —NH— or —N($C_{1-6}$ alkyl)-;

each n is independently selected from 1 to 10;

$R^1$ to $R^{24}$ are each independently selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, halo, —CN, —$NO_2$, —$C_1$-$C_{10}$ haloalkyl, —$C_1$-$C_{10}$ dihaloalkyl, —$C_1$-$C_{10}$ trihaloalkyl, —$COR^{28}$, —$CO_2R^{28}$, —$OR^{28}$, —$SR^{28}$, —$N(R^{28})_2$, —$NR^{28}OR^{28}$, —$ON(R^{28})_2$, —$SOR^{28}$, —$SO_2R^{28}$, —$SO_3R^{28}$, —$SON(R^2)_2$, —$SO_2N(R^{28})_2$, —$SO_3N(R^{28})_2$, —$P(R^{28})_3$, —$P(O)(R^{28})_3$, —$OSi(R^{28})_3$, —$OB(R^{28})_2$, —$C(Z)R^{28}$ and —$ZC(Z)R^{28}$;

$R^{28}$ is selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, —$C_6$-$C_{14}$ aryl, —$C_5$-$C_{14}$ heteroaryl, —$C_3$-$C_{14}$ heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl; or one or more of $R^1$ (or $R^2$) is connected to $R^3$ (or $R^4$), and/or $R^3$ (or $R^4$) is connected to $R^5$ (or $R^6$), and/or $R^5$ (or $R^6$) is connected to $R^7$, and/or $R^7$ is connected to $R^8$ (or $R^9$), and/or $R^8$ (or $R^9$) is connected to $R^{10}$ (or $R^{11}$), and/or $R^{10}$ (or $R^{11}$) is connected to $R^{12}$, and/or $R^{12}$ is connected to $R^{13}$ (or $R^{14}$), and/or $R^{13}$ is connected to $R^{14}$, and/or $R^{13}$ (or $R^{14}$) is connected to $R^{15}$, and/or $R^{15}$ is connected to $R^{17}$, and/or $R^{18}$ (or $R^{19}$ or $R^{20}$) is connected to $R^{22}$ (or $R^{21}$), and/or $R^{22}$ (or $R^{21}$) is connected to $R^{23}$, and/or $R^{23}$ is connected to $R^1$ (or $R^2$), and/or $R^{24}$ is connected to $R^7$ (or $R^{16}$) or $R^8$ (or $R^9$) to form a —$C_1$-$C_8$ disubstituted (fused) saturated or unsaturated carbo- and heterocyclic rings further substituted by $R^{28}$, —(C═Z)$R^{28}$ and —Z(C═Z)$R^{28}$; or one or more of $R^1$ (or $R^2$) is connected to $R^3$ (or $R^4$), $R^3$ (or $R^4$) is connected to $R^5$ (or $R^6$), $R^5$ (or $R^6$) is connected to $R^7$, $R^7$ is connected to $R^{24}$, $R^8$ (or $R^9$) is connected to $R^{10}$ (or $R^{11}$), $R^{16}$ is connected to $R^{24}$, $R^{22}$ (or $R^{21}$) is connected to $R^{23}$, $R^{23}$ is connected to $R^1$ (or $R^2$), $R^{24}$ is connected to $R^7$ (or $R^{16}$) or $R^8$ (or $R^9$) to form a double bond, an epoxide or a thioepoxide; or one or more of $R^1$ and $R^2$, $R^3$ and $R^4$, $R^5$ and $R^6$, $R^8$ and $R^9$, $R^{10}$ and $R^{11}$, $R^{18}$ and $R^{19}$ (or $R^{18}$ and $R^{20}$), $R^{21}$ and $R^{22}$ form a double bond to Z, and Z is selected from sulfur, oxygen and —NH— or —N($C_1$-$C_6$ alkyl)-;

or a pharmaceutically, agriculturally or pesticidally acceptable salt thereof.

In some embodiments, when any one or more of $R^1$ to $R^{24}$ is —$C_2$-$C_{20}$ alkenyl, the alkenyl units may be singular, multiple, allenyl and/or conjugated or skipped.

In other embodiments, where any one or more of $R^1$ to $R^{10}$ is —$C_2$-$C_{20}$ alkynyl, one or more of $R^1$ to $R^{10}$ may further comprise an aryl or heteroaryl group.

In still other embodiments when any one or more of $R^1$ to $R^{24}$ is —$C_2$-$C_{20}$ alkynyl, the alkynyl units may be singular or multiple alkynyl units.

In another aspect of the invention, there is provided a compound of formula II (II)

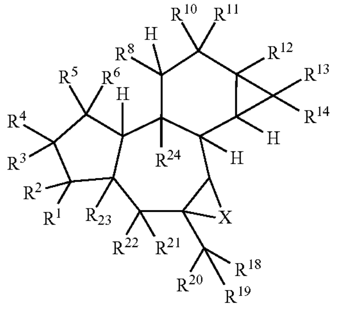

wherein:

X is selected from —O—, —S— and —$NR^{25}$—;

$R^1$ and $R^2$ are independently selected from hydrogen, —OH, —$OC_1$-$C_{10}$ alkyl, —$OC_2$-$C_{10}$ alkenyl, —$OC_2$-$C_{10}$ alkynyl, —Ocycloalkyl, —OC(O)$C_1$-$C_{10}$ alkyl, —OC(O)$C_2$-$C_{10}$ alkenyl, —OC(O)$C_2$-$C_{10}$ alkynyl, —OC(O)cycloalkyl, —OC(O)heterocyclyl, —OC(O)heteroaryl, —OC(O)NH$C_1$-$C_{10}$ alkyl, —OC(O)NH$C_2$-$C_{10}$ alkenyl, —OC(O)NH$C_2$-$C_{10}$ alkynyl, —OC(O)NHcycloalkyl, —OC(O)NHaryl, —OC(O)NHheterocyclyl, —OC(O)NHheteroaryl, —OC(S)NH$C_1$-$C_{10}$ alkyl, —OC(S)NH$C_2$-$C_{10}$ alkenyl, —OC(S)NH$C_2$-$C_{10}$ alkynyl, —OC(S)NHcycloalkyl, —OC(S)

NHaryl, —OC(S)NHheterocyclyl, —OC(S)NHheteroaryl or $R^1$ and $R^2$ taken together are =O, =S, =NH or =N($C_1$-$C_6$ alkyl);

$R^3$ is hydrogen, —$C_1$-$C_{10}$ alkyl, —$C_2$-$C_{10}$ alkenyl or —$C_2$-$C_{10}$ alkynyl;

$R^4$ and $R^5$ are each hydrogen, —$C_1$-$C_{10}$ alkyl, —$C_2$-$C_{10}$ alkenyl, —$C_2$-$C_{10}$ alkynyl, —OH, —O$C_1$-$C_{10}$ alkyl, —O$C_2$-$C_{10}$ alkenyl, —O$C_2$-$C_{10}$ alkynyl, —Ocycloalkyl, —OC(O)$C_1$-$C_{10}$ alkyl, —OC(O)$C_2$-$C_{10}$ alkenyl, —OC(O)$C_2$-$C_{10}$ alkynyl, —OC(O)cycloalkyl, —OC(O)aryl, —OC(O)heterocyclyl, —OC(O)heteroaryl, —OC(O)NH$C_1$-$C_{10}$ alkyl, —OC(O)NH$C_2$-$C_{10}$ alkenyl, —OC(O)NH$C_2$-$C_{10}$ alkynyl, —OC(O)NHcycloalkyl, —OC(O)NHaryl, —OC(O)NHheterocyclyl, —OC(O)NHheteroaryl, —OC(S)NH$C_1$-$C_{10}$ alkyl, —OC(S)NH$C_2$-$C_{10}$ alkenyl, —OC(S)NH$C_2$-$C_{10}$ alkynyl, —OC(S)NHcycloalkyl, —OC(S)NHaryl, —OC(S)NHheterocyclyl, —OC(S)NHheteroaryl, F, Cl, Br, I, —CN, —$NO_2$ or N($R^{25}$)$_2$, or $R^4$ and $R^5$ taken together form a double bond or are —O—, —S—, —$NR^{25}$ or —$CR^{26}R^{27}$—;

$R^6$ is selected from hydrogen, —$C_1$-$C_{10}$ alkyl, —$C_2$-$C_{10}$ alkenyl and —$C_2$-$C_{10}$ alkynyl;

$R^8$ is selected from hydrogen, —$C_1$-$C_{10}$ alkyl, —$C_2$-$C_{10}$ alkenyl and —$C_2$-$C_{10}$ alkynyl;

$R^{10}$ is selected from hydrogen, —$C_1$-$C_{10}$ alkyl, —$C_2$-$C_{10}$ alkenyl and —$C_2$-$C_{10}$ alkynyl;

$R^{11}$ is selected from —OH, —O$C_1$-$C_{20}$ alkyl, —O$C_2$-$C_{20}$ alkenyl, —O$C_2$-$C_{20}$ alkynyl, —OC(O)cycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)heterocyclyl, —OC(O)heteroaryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(O)NHheterocyclyl, —OC(O)NHheteroaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl, —OC(S)NHaryl, —OC(S)NHheterocyclyl, —OC(S)NHheteroaryl or $R^{10}$ and $R^{11}$ taken together form a carbonyl group (=O);

$R^{12}$ is selected from —OH, —O$C_1$-$C_{20}$ alkyl, —O$C_2$-$C_{20}$ alkenyl, —O$C_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)heterocyclyl, —OC(O)heteroaryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(O)NHheterocyclyl, —OC(O)NHheteroaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl, —OC(S)NHaryl, —OC(S)NHheterocyclyl, —OC(S)NHheteroaryl;

$R^{13}$ and $R^{14}$ are independently selected from hydrogen and —$C_1$-$C_{10}$ alkyl;

$R^{18}$ is selected from $C_1$-$C_{20}$ alkyl, —$C_2$-$C_{20}$ alkenyl, —$C_2$-$C_{20}$ alkynyl, —OH, —O$C_1$-$C_{20}$ alkyl, —O$C_2$-$C_{20}$ alkenyl, —O$C_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)heterocyclyl, —OC(O)heteroaryl, —NH$C_1$-$C_{20}$ alkyl, —NH$C_2$-$C_{20}$ alkenyl, —NH$C_2$-$C_{20}$ alkynyl, —NHcycloalkyl, —NHaryl, —NHheterocyclyl, —NHheteroaryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(O)NHheterocyclyl, —OC(O)NHheteroaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl, —OC(S)NHaryl, —OC(S)NHheterocyclyl, —OC(S)NHheteroaryl;

$R^{19}$ and $R^{20}$ are independently selected from hydrogen, —$C_1$-$C_6$ alkyl, —$C_2$-$C_6$ alkenyl, —$C_2$-$C_6$ alkynyl, —OH, —O$C_1$-$C_6$ alkyl, —O$C_2$-$C_6$ alkenyl, —O$C_2$-$C_6$ alkynyl, —Ocycloalkyl, —OC(O)$C_1$-$C_6$ alkyl, —OC(O)$C_2$-$C_6$ alkenyl, —OC(O)$C_2$-$C_6$ alkynyl, —OC(O)cycloalkyl, —OC(O)aryl, —OC(O)heterocyclyl, —OC(O)heteroaryl or $R^{19}$ and $R^{20}$ taken together form a carbonyl or thiocarbonyl group;

$R^{21}$ is selected from hydrogen, —$C_1$-$C_{10}$ alkyl, —$C_2$-$C_{10}$ alkenyl and —$C_2$-$C_{10}$ alkynyl;

$R^{22}$ is selected from hydrogen, —OH, —O$C_1$-$C_{20}$ alkyl, —O$C_2$-$C_{20}$ alkenyl, —O$C_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)heterocyclyl, —OC(O)heteroaryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(O)NHheterocyclyl, —OC(O)NHheteroaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl, —OC(S)NHaryl, —OC(S)NHheterocyclyl, —OC(S)NHheteroaryl or $R^{21}$ and $R^{22}$ taken together form a carbonyl group;

$R^{23}$ is selected from hydrogen, —OH, —O$C_1$-$C_{20}$ alkyl, —O$C_2$-$C_{20}$ alkenyl, —O$C_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)heterocyclyl, —OC(O)heteroaryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(O)NHheterocyclyl, —OC(O)NHheteroaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl, —OC(S)NHaryl, —OC(S)NHheterocyclyl, —OC(S)NHheteroaryl;

$R^{24}$ is selected from hydrogen, —OH, —O$C_1$-$C_{20}$ alkyl, —O$C_2$-$C_{20}$ alkenyl, —O$C_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)heterocyclyl, —OC(O)heteroaryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(O)NHheterocyclyl, —OC(O)NHheteroaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl, —OC(S)NHaryl, —OC(S)NHheterocyclyl, —OC(S)NHheteroaryl;

$R^{25}$ is selected from hydrogen and —$C_1$-$C_{10}$ alkyl;

$R^{26}$ and $R^{27}$ are independently selected from hydrogen, —$C_1$-$C_{10}$ alkyl, —OH, —O$C_1$-$C_{10}$ alkyl;

wherein each alkyl, alkenyl, alkynyl, cycloalkyl, aryl, heterocyclyl and heteroaryl is optionally substituted;

and geometric isomers or stereoisomers thereof and pharmaceutically, agriculturally or pesticidally acceptable salts thereof.

In one embodiment, the taglienone derivative of formula (II) is a compound of formula (III)

(III)

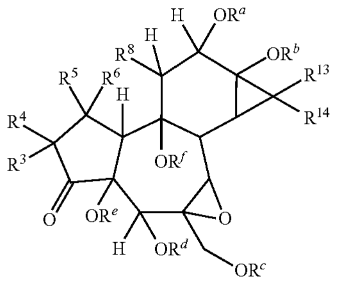

wherein:

$R^3$ is hydrogen, —$C_1$-$C_6$ alkyl or —$C_2$-$C_6$ alkenyl;

$R^4$ and $R^5$ are each independently hydrogen, —$C_1$-$C_6$ alkyl, —$C_2$-$C_6$ alkenyl, —OH, —O$C_1$-$C_6$ alkyl, —O$C_2$-$C_6$ alkenyl, —$OC(O)C_1$-$C_6$ alkyl, —$OC(O)C_2$-$C_6$ alkenyl, —OC(O)aryl, —OC(O)heterocyclyl, —OC(O)heteroaryl, F, Cl, Br or I, or $R^4$ and $R^5$ taken together form a double bond or are —O—;

$R^6$ is hydrogen, —$C_1$-$C_6$ alkyl or —$C_2$-$C_6$ alkenyl;

$R^8$ is hydrogen, —$C_1$-$C_6$ alkyl or —$C_2$-$C_6$ alkenyl;

$R^{13}$ and $R^{14}$ are each independently hydrogen or —$C_1$-$C_6$ alkyl;

$R^a$, $R^b$, $R^C$, $R^d$, $R^e$ and $R^f$ are each independently selected from hydrogen, —$C_1$-$C_{20}$ alkyl, —$C_2$-$C_{20}$ alkenyl, —$C_2$-$C_{20}$ alkynyl, —$C(O)C_1$-$C_{20}$ alkyl, —$C(O)C_2$-$C_{20}$ alkenyl, —$C(O)C_2$-$C_{20}$ alkynyl, —C(O)cycloalkyl, —C(O)aryl, —C(O)heterocyclyl, —C(O)heteroaryl, —$C(O)NHC_1$-$C_{20}$ alkyl, —$C(O)NHC_2$-$C_{20}$ alkenyl, —$C(O)NHC_2$-$C_{20}$ alkynyl, —C(O)NHcycloalkyl, —C(O)NHaryl, —C(O)NHheterocyclyl, —C(O)NHheteroaryl, —$C(S)NHC_1$-$C_{20}$ alkyl, —$C(S)NHC_2$-$C_{20}$ alkenyl, —$C(S)NHC_2$-$C_{20}$ alkynyl, —C(S)NHcycloalkyl, —C(S)NHaryl, —C(S)NHheterocyclyl and —C(S)NHheteroaryl;

wherein each alkyl, alkenyl, aryl, heterocyclyl and heteroaryl group is optionally substituted;

or geometric isomers or stereoisomers and pharmaceutically, agriculturally or pesticidally acceptable salts thereof.

In a preferred embodiment, the compound of formula (II) is a compound of formula IV (IV)

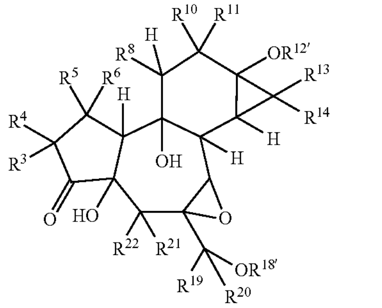

wherein:

$R^3$ is hydrogen, —$C_1$-$C_6$ alkyl or —$C_2$-$C_6$ alkenyl;

$R^4$ and $R^5$ are each independently hydrogen, —$C_1$-$C_6$ alkyl, —$C_2$-$C_6$ alkenyl, —OH, —$OC_1$-$C_6$ alkyl, —$OC_2$-$C_6$ alkenyl, —$OC(O)C_1$-$C_6$ alkyl, —$OC(O)C_2$-$C_6$ alkenyl, —OC(O)aryl, —OC(O)heterocyclyl, —OC(O)heteroaryl, F, Cl, Br or I, or $R^4$ and $R^5$ taken together form a double bond or are —O—;

$R^6$ is hydrogen, —$C_1$-$C_6$ alkyl or —$C_2$-$C_6$ alkenyl;

$R^8$ is hydrogen, —$C_1$-$C_6$ alkyl or —$C_2$-$C_6$ alkenyl;

$R^{10}$ is hydrogen;

$R^{11}$ is hydroxy, —$OC_1$-$C_{20}$ alkyl, —$OC_2$-$C_{20}$ alkenyl, —$OC(O)C_1$-$C_{20}$ alkyl, —$OC(O)C_2$-$C_{20}$ alkenyl, —OC(O)aryl, —OC(O)heterocyclyl, —OC(O)heteroaryl; or $R^{10}$ and $R^{11}$ taken together form a carbonyl group;

$R^{12'}$ is hydrogen, —$C_1$-$C_{20}$ alkyl, —$C_2$-$C_{20}$ alkenyl, —$C(O)C_1$-$C_{20}$ alkyl, —$C(O)C_2$-$C_{20}$ alkenyl, —C(O)aryl, —C(O)heterocyclyl or —C(O)heteroaryl;

$R^{13}$ and $R^{14}$ are each independently hydrogen or —$C_1$-$C_6$ alkyl;

$R^{18'}$ is hydrogen, —$C_1$-$C_6$ alkyl, —$C_2$-$C_6$ alkenyl, —$C(O)C_1$-$C_6$ alkyl, —$C(O)C_2$-$C_6$ alkenyl, —C(O)aryl, —C(O)heterocyclyl or —C(O)heteroaryl;

$R^{19}$ and $R^{20}$ are independently selected from hydrogen, —OH, —$OC_1$-$C_6$ alkyl, —$OC_2$-$C_6$ alkenyl or $R^{19}$ and $R^{20}$ taken together form a carbonyl group;

$R^{21}$ is hydrogen;

$R^{22}$ is hydroxy, —$OC_1$-$C_6$ alkyl, —$OC_2$-$C_6$ alkenyl, —$OC(O)C_1$-$C_6$ alkyl, —$OC(O)C_2$-$C_6$ alkenyl, —OC(O)aryl, —OC(O)heterocyclyl, —OC(O)heteroaryl or $R^{21}$ and $R^{22}$ taken together form a carbonyl group;

wherein each alkyl, alkenyl, aryl, heterocyclyl or heteroaryl is optionally substituted;

and geometric isomers or stereoisomers thereof and pharmaceutically, agriculturally or pesticidally acceptable salts thereof.

In preferred embodiments of formula II at least one of the following applies:

$R^1$ and $R^2$ are independently selected from hydrogen or —OH or taken together form a carbonyl group;

$R^3$ is hydrogen or —$C_1$-$C_3$ alkyl, especially hydrogen or methyl;

$R^4$ and $R^5$ are each hydrogen or $R^4$ and $R^5$ form a double bond or are —O—;

$R^6$ is hydrogen or —$C_1$-$C_3$ alkyl, especially hydrogen;

$R^5$ is hydrogen or —$C_1$-$C_3$ alkyl, especially hydrogen or methyl;

$R^{10}$ is hydrogen;

$R^{11}$ is —OH, —$OC_1$-$C_{20}$ alkyl, —$OC_2$-$C_{20}$ alkenyl, —$OC(O)C_1$-$C_{20}$ alkyl, —$OC(O)C_2$-$C_{20}$ alkenyl, especially —$OC(O)C_1$-$C_{15}$ alkyl or —$OC(O)C_2$-$C_{15}$ alkenyl, where each alkenyl group has one or more double bonds where the double bonds may be isolated or conjugated;

$R^{12}$ is —OH, —$OC_1$-$C_{20}$ alkyl, —$OC_2$-$C_{20}$ alkenyl, —$OC(O)C_1$-$C_{20}$ alkyl or —$OC(O)C_2$-$C_{20}$ alkenyl, especially —$OC(O)C_1$-$C_{10}$ alkyl, —$OC(O)C_2$-$C_{10}$ alkenyl;

$R^{13}$ and $R^{14}$ are each independently hydrogen or —$C_1$-$C_3$ alkyl, especially hydrogen or methyl, more especially where both $R^{13}$ and $R^{14}$ are methyl;

$R^{18}$ is —OH, —$OC_1$-$C_6$ alkyl, —$OC_2$-$C_6$ alkenyl, —$OC(O)C_1$-$C_6$ alkyl or —$OC(O)C_2$-$C_6$ alkenyl, especially —OH or —$OC(O)C_1$-$C_3$ alkyl;

$R^{19}$ and $R^{20}$ are independently selected from hydrogen, —OH, —$OC_1$-$C_3$ alkyl, —$OC_2$-$C_3$ alkenyl or $R^{19}$ and $R^{20}$ taken together form a carbonyl group, especially hydrogen, hydroxy or together a carbonyl group;

$R^{21}$ is hydrogen;

$R^{22}$ is —OH, —$OC_1$-$C_6$ alkyl, —$OC_2$-$C_6$ alkenyl, —$OC(O)C_1$-$C_6$ alkyl or —$OC(O)C_2$-$C_6$ alkenyl, especially —OH or —$OC(O)C_1$-$C_3$ alkyl;

$R^{23}$ is —OH or —$OC_1$-$C_3$ alkyl, especially —OH;

$R^{14}$ is —OH or —$OC_1$-$C_3$ alkyl, especially —OH.

In one particular embodiment, the compound is a compound of formula II is 12-tigloyl-13-(2-methylbutanoyl)-6,7-epoxy-4,5,9,12,13,20-hexahydroxy-1-tigliaen-3-one (EBI-46):

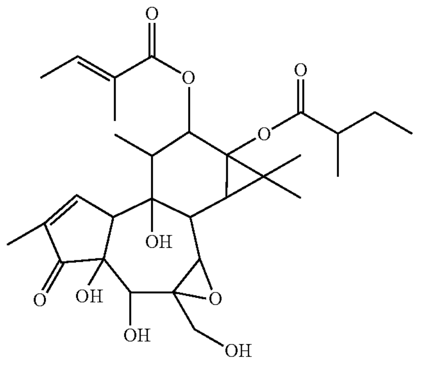

In another embodiment the compound is 12,13-di-(2-methylbutanoyl)-6,7-epoxy-4,5,9,12,13,20-hexahydroxy-tigliaen-3-one (EBI-47):

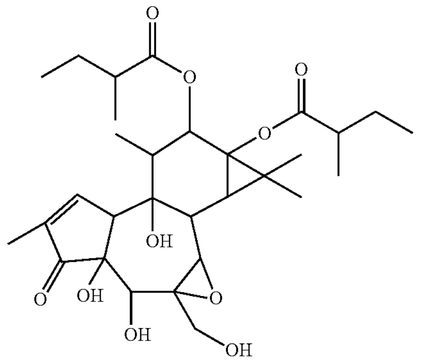

In yet another particular embodiment, the compound is 12-(dodeca-2,4,6-trienoyl)-13-(2-methylbutanoyl)-6,7-epoxy-4,5,9,12,13,20-hexahydroxy-1-tigliaen-3-one (EBI-59):

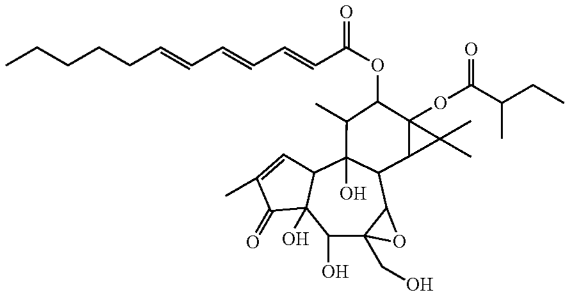

In still yet another particular embodiment, the compound is 12-(deca-2,4-dienoyl)-6,7-epoxy-4,5,9,12,13,20-hexahydroxy-1-tigliaen-3-one (EBI-61):

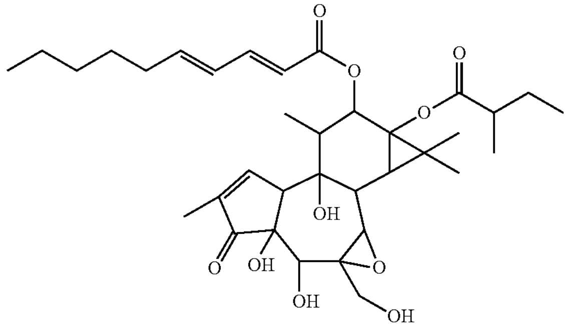

In yet another embodiment, the compounds is 12,13-di-(2-methylbutanoyl)-1,2-2H-1,2,6,7-diepoxy-6-carboxy-4,5,9,12,13-pentahydroxy-tigliaen-3-one:

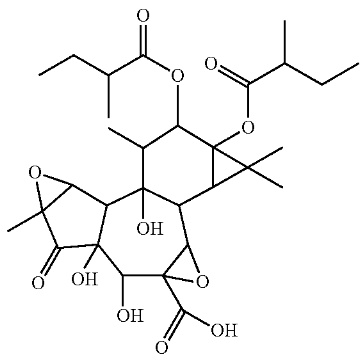

In yet another embodiment, the compound is 12,13-di-(2-methylbutanoyl)-5,20-di-acetoyl-4,5,9,12,13,20-hexahydroxy-tigliaen-3-one:

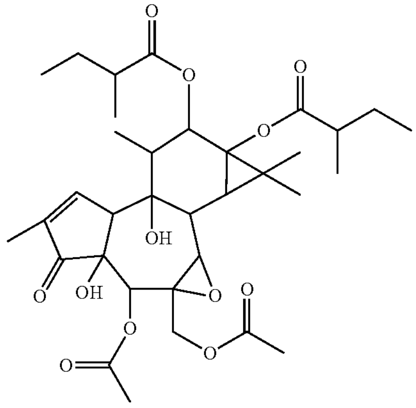

The term "alkyl" refers to optionally substituted linear and branched hydrocarbon groups having 1 to 20 carbon atoms. Where appropriate, the alkyl group may have a specified number of carbon atoms, for example, —$C_1$-$C_6$ alkyl which includes alkyl groups having 1, 2, 3, 4, 5 or 6 carbon atoms in linear or branched arrangements. Non-limiting examples of alkyl groups include methyl, ethyl, propyl, isopropyl, butyl, s- and t-butyl, pentyl, 2-methylbutyl, 3-methylbutyl, hexyl, 2-methylpentyl, 3-methylpentyl, 4-methylpentyl, 2-ethylbutyl, 3-ethylbutyl, heptyl, octyl, nonyl, decyl, undecyl, dodecyl, tridecyl, tetradecyl, pentadecyl.

The term "alkenyl" refers to optionally substituted, unsaturated linear or branched hydrocarbons, having 2 to 20 carbon atoms and having at least one double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, pentenyl, hexenyl, hept-1,3-diene, hex-1,3-diene, non-1,3,5-triene and the like.

The term "alkynyl" refers to optionally substituted unsaturated linear or branched hydrocarbons, having 2 to 20 carbon atoms, having at least one triple bond. Where appropriate, the alkynyl group may have a specified number of carbon atoms, for example, $C_2$-$C_6$ alkynyl which includes alkynyl groups having 2, 3, 4, 5 or 6 carbon atoms in linear or branched arrangements. Non-limiting examples include ethynyl, propynyl, butynyl, pentynyl and hexynyl.

The terms "cycloalkyl" and "carbocyclic" refer to optionally substituted saturated or unsaturated mono-cyclic, bicyclic or tricyclic hydrocarbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

"Aryl" means a $C_6$-$C_{14}$ membered monocyclic, bicyclic or tricyclic carbocyclic ring system having up to 7 atoms in each ring, wherein at least one ring is aromatic. Examples of aryl groups include, but are not limited to, phenyl, naphthyl, tetrahydronaphthyl, indanyl and biphenyl. The aryl may comprise 1-3 benzene rings. If two or more aromatic rings are present, then the rings may be fused together, so that adjacent rings share a common bond.

"Heterocyclic" or "heterocyclyl" refers to a non-aromatic ring having 3 to 8 atoms in the ring and of those atoms 1 to 4 are heteroatoms, said ring being isolated or fused to a second ring selected from 3- to 7-membered alicyclic ring containing 0 to 4 heteroatoms, wherein said heteroatoms are independently selected from O, N and S. Heterocyclic includes partially and fully saturated heterocyclic groups. Heterocyclic systems may be attached to another moiety via any number of carbon atoms or heteroatoms of the radical and may be both saturated and unsaturated, which includes all forms of carbohydrate moieties. Non-limiting examples of heterocyclic include pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

The term "heteroaryl" as used herein means a stable monocyclic or bicyclic ring of up to 7 atoms in each ring, wherein at least one ring is aromatic and at least one ring contains from 1-4 heteroatoms, selected from sulfur, oxygen and nitrogen. Heteroaryl includes, but is not limited to, oxazolyl, thiazolyl, thienyl, furyl, 1-isobenzofuranyl, pyrrolyl, imidazolyl, pyrazolyl, isothiazolyl, isooxazolyl, pyridyl, pyrazinyl, pyrimidinyl, pyradazinyl, indolizinyl, isoindolyl, indolyl, purinyl, phthalazinyl, 1,2,3-triazolyl, 1,2,4-triazolyl, 1,2,3-oxadiazoyl, 1,2,4-oxadiazolyl, 1,2,5-oxadiazolyl, 1,3,4-oxadiazolyl, 1,2,3,4-oxatriazolyl, 1,2,3,5-oxatriazolyl, 1,3,5-triazinyl, 1,2,4-triazinyl, 1,2,3-triazinyl, benzofuranyl, isobenzofuranyl, thionaphthenyl, isothionaphthenyl, indoleninyl, 2-isobenzazolyl, 1,5-pyrindinyl, pyrano[3,4-b]pyrrolyl, isoindazolyl, indoxazinyl, benzoxazolyl, quinolinyl, isoquinolinyl, cinnolinyl, quinazolinyl, naphthyridinyl, pyrido[3,4-b]pyridinyl, pyrido[3,2-b]pyridinyl, pyrido[4,3-b]pyridinyl, acridinyl, carbazolyl, quinaoxalinyl, pyrazolyl, benzotriazolyl, thiophenyl, isoquinolinyl, pyridinyl, tetrahydroquinolinyl, benzazepinyl, benzodioxanyl, benzoxepinyl, benzodiazepinyl, benzothiazepinyl and benzothiepinyl and the like.

Each alkyl, alkenyl, alkynyl, cycloalkyl, aryl, heterocyclyl and heteroaryl group are optionally substituted with one or more substituent independently selected from —F, —Cl, —Br, —I, —CN, —$CF_3$, —$CO_2R^{28}$, —$COR^{28}$, —$OR^{28}$, —$SR^{28}$, —$N(R^{28})_2$, —$NO_2$, —$NR^{28}OR^{28}$, —$ON(R^{28})_2$, —$SOR^{28}$, —$SO_2R^{28}$, —$SO_3R^{28}$, —$SON(R^{28})_2$, $SON(R^{28})_2$, —$SO_3N(R^{28})_2$, —$P(R^{28})_3$, —$P({=}O)(R^{28})_3$, —$OSi(R^{28})_3$, —$OB(R^{28})_2$ wherein $R^{28}$ is as defined above.

Yet another aspect of the invention provides a pharmaceutically, agriculturally or pesticidally acceptable salt of a compound of formula (I) or formula (II).

The terms "pharmaceutically acceptable salts", "agriculturally acceptable salts" and "pesticidally acceptable salts" as used herein refer to salts which are toxicologically safe for systemic or topical administration to a human or animal or those that may be safely applied to a plant or environment. The pharmaceutically, agriculturally or pesticidally acceptable salts may be selected from the group including, but not limited to, alkali and alkali earth, ammonium, aluminium, iron, amine, glucosamine, chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, pamoate, pectinate and s-methyl methionine salts, piperazine and the like.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be obtained by isolation from natural sources, by asymmetric synthesis, for example using chiral intermediates, or by chiral resolution. The compounds of the invention may exist as geometrical isomers. The invention also relates to compounds in substantially pure cis (Z) or trans E) forms or mixtures thereof.

The compounds of the present invention may be obtained by isolation from a plant or plant part, or by derivatisation of the isolated compound, or by derivatisation of a related compound.

Yet another aspect of the invention provides a method of isolating one or more compounds of formula (I) to formula (IV), which method includes the step of extracting said one or more compounds from a plant or plant part.

Preferably, the plant is of the genus *Fontainea* or *Hylandia*.

Preferably the species is *Fontainea pancheri, Fontainea australis, Fontainea borealis, Fontainea fugax, Fontainea oraria, Fontainea picrosperma, Fontainea rostrata, Fontainea subpapuana, Fontainea venosa* or *Hylandia dockrillii*, especially *Fontainea picrosperma, Fontainea venosa* or *Hylandia dockrillii.*

The parts of the plant may include fruit, seed, bark, leaf, flower, roots and wood.

Preferably the extract is obtained from the seed, bark and/or flowers.

For example, the biomass obtained from seeds, leaves, flowers and bark of the plant is subject to initial solvent extraction, for example with a polar solvent such as methanol. The initial extraction is then concentrated and diluted with water and subject to extraction with a second solvent, for example, ethyl acetate. The solvent samples from the second extraction are pooled and subject to separation by preparative HPLC fractionation. The fractions are analysed by analytical HPLC and pooled according to the retention time of compounds found in the samples. The pooled fractions are weighed, bioassayed and analysed by analytical HPLC. Further fractionation using one or more preparative HPLC is performed to isolate specific compounds. Each compound is bioassayed and its structure identified by UV, NMR and mass spectrometric techniques.

Other compounds of the invention may be obtained by derivatising compounds isolated from plants or parts of plants, especially from the genus *Fontainea*, especially from the species *Fontainea picrosperma*, especially the seeds, bark and/or flowers of *Fontainea picrosperma.*

Derivatives of the natural compounds can be obtained by techniques known in the art. For example, hydroxy groups may be oxidised, to ketones, aldehydes or carboxylic acids by exposure to oxidising agents such as chromic acid, Jones' reagent, $KMnO_4$, peracids such as mCPBA (metachloroperbenzoic acid) or dioxiranes such as dimethyldioxirane (DMDO) and methyl(trifluoromethyl)dioxirane (TFDO). Oxidising agents may be chosen such that other functional groups in the molecule are or are not also oxidised. For example, a primary alcohol may be selectively oxidised to an aldehyde or carboxylic acid in the presence of secondary alcohols using reagents such as $RuCl_2(PPh_3)_3$-benzene. Secondary alcohols may be selectively oxidised to ketones in the presence of a primary alcohol using $Cl_2$-pyridine or $NaBrO_3$-ceric-ammonium nitrate. Alcohols may be oxidised in the presence of double and triple bonds and without epimerisation at adjacent stereocentres using Jones' reagent with our without Celite (or ammonium chloride). Alternatively, reagents chosen may be less selective resulting in oxidation at more than one functional group.

Hydroxy groups may also be derivatised by etherification or acylation. For example, ethers may be prepared by formation of an alkoxide ion in the presence of base and reacting the alkoxide with an appropriate alkylhalide, alkenylhalide, alkynylhalide or arylhalide. Similarly acylation may be achieved by formation of an alkoxide ion and reaction with an appropriate carboxylic acid or activated carboxylic acid (such as an anhydride).

Hydroxy groups may be derivatised to provide carbamates or thiocarbamates by reaction with isocyanates or isothiocyanates.

Carboxylic acids can be converted to thioesters or thioamides using Lawesson's reagent.

Acyl groups may be hydrolysed to provide alcohols by acid or base hydrolysis as known in the art and those alcohols can be derivatised further as above.

Ketones may be reduced to secondary alcohols by reducing agents such as lithium aluminium hydride and other metal hydrides without reducing double bonds, including α-unsaturated ketones.

Double bonds and triple bonds may be reduced to single bonds using catalytic reduction, for example, $H_2$/Pd. Double bonds may also be oxidised to epoxides using oxidising agents such as per acids, for example mCPBA or dioxiranes, such as DMDO and TFDO. Double bonds may also be subject to addition reactions to introduce substituents such as halo groups, hydroxy or alkoxy groups and amines.

A person skilled in the art would be able to determine suitable conditions for obtaining derivatives of isolated compounds, for example, by reference to texts relating to synthetic methodology, examples of which are Smith M. B. and March J., March's Advanced Organic Chemistry, Fifth Edition, John Wiley & Sons Inc., 2001 and Larock R. C., Comprehensive Organic Transformations, VCH Publishers Ltd., 1989. Furthermore, selective manipulations of functional groups may require protection of other functional groups. Suitable protecting groups to prevent unwanted side reactions are provided in Green and Wuts, Protective Groups in Organic Synthesis, John Wiley & Sons Inc., 3rd Edition, 1999.

Still yet another aspect of the invention provides a pharmaceutical composition for treatment or prophylaxis of a disease or condition comprising an effective amount of one or more compounds of formula (I) or formula (II), or a pharmaceutically acceptable salt thereof, and a pharmaceutically acceptable carrier, diluent and/or excipient.

Dosage form and rates for pharmaceutical use and compositions are readily determinable by a person of skill in the art.

Dosage forms include tablets, dispersions, suspensions, injections, solutions, syrups, troches, capsules, suppositories, aerosols, transdermal patches, creams, gels and the like. These dosage forms may also include injecting or implanting devices designed specifically for, or modified to, controlled release of the pharmaceutical composition. Controlled release of the therapeutic agent may be effected by coating the same, for example, with hydrophobic polymers including acrylic resins, waxes, higher aliphatic alcohols, polyactic and polyglycolic acids and certain cellulose derivates such as hydroxypropylmethyl cellulose. In addition, the controlled release may be affected by using other polymer matrices, liposomes and/or microspheres.

Pharmaceutically acceptable carriers and acceptable carriers for systemic administration may also be incorporated into the compositions of this invention.

Suitably, the pharmaceutical composition comprises a pharmaceutically acceptable excipient or an acceptable excipient. By "pharmaceutically acceptable excipient" is meant a solid or liquid filler, diluent or encapsulating substance that may be safely used. Depending upon the particular route of administration, a variety of carriers, well known in the art may be used. These carriers or excipients may be selected from a group including sugars, starches, cellulose and its derivates, malt, gelatine, talc, calcium sulphate, vegetable oils, synthetic oils, polyols, alginic acid, phosphate buffered solutions, emulsifiers, isotonic saline, and pyrogen-free water.

Any suitable route of administration may be employed for providing a human or non-human patient with the pharmaceutical composition of the invention. For example, oral, rectal, parenteral, sublingual, buccal, intravenous, intraarticular, intramuscular, intra-dermal, subcutaneous, inhalational, intraocular, intraperitoneal, intracerebroventricular, transdermal and the like may be employed.

Pharmaceutical compositions of the present invention suitable for administration may be presented in discrete units such as vials, capsules, sachets or tablets each containing a predetermined amount of one or more pharmaceutically active compounds of the invention, as a powder or granules or as a solution or a suspension in an aqueous liquid, a non-aqueous liquid, an oil-in-water emulsion or a water-in-oil emulsion or as a solution or suspension in a cream or gel. Such compositions may be prepared by any of the method of pharmacy but all methods include the step of bringing into association one or more pharmaceutically active compounds of the invention with the carrier which constitutes one or more necessary ingredients. In general, the compositions are prepared by uniformly and intimately admixing the agents of the invention with liquid carriers or finely divided solid carriers or both, and then, if necessary, shaping the product in to the desired presentation.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

The active compounds of formula (I) and formula (II) and of the compositions of this invention are present in an amount sufficient to prevent, inhibit or ameliorate a disease or condition. Suitable dosages of the compounds of formula (I) or formula (II) and the pharmaceutical compositions containing such may be readily determined by those skilled in the art.

In a still further aspect of the invention, there is provided a method of treating or prophylaxis of a disease or condition comprising administering to a subject in need of such treatment an effective amount of one or more compounds according to formula (I) or formula (II), or a pharmaceutically acceptable salt thereof.

In yet another aspect of the invention, there is provided the use of one or more of the compounds according to formula (I) or formula (II), or a pharmaceutically acceptable salt thereof, in the manufacture of a medicament for the treatment or prophylaxis of a disease or condition.

Non-limiting examples of a diseases or a condition are a bacterial infection, a parasitic infestation and a cell proliferative disorder. In non-limiting embodiments compounds of formula (I) or formula (II) have one or more activities selected from antiparasitic activity (e.g. against an endoparasite and/or an ectoparasite, such as, *Haemonchus contortus*), antibiotic activity (e.g. against *Bacillus subtilis*), antiprotozoal activity (e.g. against *Giardia* sp. Portland) cytotoxic activity (e.g. against a basal cell carcinoma and/or a squamous cell carcinoma and/or a melanoma and/or antitumour activity (e.g. against a leukemia, a melanoma, a prostate cancer, a breast cancer, an ovarian cancer and/or other solid tumour cancers).

In one aspect of the invention, there is provided a method of treating or preventing a bacterial infection in a subject comprising administering to a subject a compound of formula (I) or formula (II) or a pharmaceutically acceptable salt thereof.

In preferred embodiments, the compound of formula (I) and formula (II) is 12-tigloyl-13-(2-methylbutanoyl)-6,7-epoxy-4,5,9,12,13,20-hexahydroxy-1-tigliaen-3-one (EBI-46).

The bacterial infection may be caused by a Gram positive or Gram negative bacteria, especially a Gram positive bacteria. Non-limiting examples of bacteria that are controlled by the compounds of the invention include bacteria of the Genus *Bacillus*, such as *B. subtilis, B. anthracis, B. cereus, B. firmis, B. licheniformis, B. megateriul, B. pumilus, B. coagulans, B. pantothenticus, B. alvei, B. brevis, B. circubins, B. laterosporus, B. inacerans, B. polymyxa, B. stearothermophilus, B. thuringiensis* and *B. sphaericus; Staphlococcus* such as *S. aureus, S. epidermidis, S. haemolyticus, S. saprophyticus; Streptococcus*, for example, *S. pyrogenes, S. pneumoniae, S. alagactiae, S. dysgalactiae, S. equisimilis, S. equi, S. zooepidemicus, S. anginosus, S. salwarius, S. milleri, S. sanguis, S. mitior, S. mutans, S. faecalis, S. faecium, S. bovis, S. equinus, S. uberus and S. avium; Aerococcus* spp., *Gemella* spp., *Corynebacterium* spp., *Listeria* spp., *Kurthia* spp., *Lactoba-*

*cillus* spp., *Erysipelothrix* spp., *Arachnia* spp., *Actinomyces* spp., *Propionibacterium* spp., *Rothia* spp., *Bifidobacterium* spp., *Clostridium* spp., *Eubacterium* spp., *Nocardia* spp. and *Mycobacterium* spp.

In another aspect of the invention there is provided a method of treating or preventing a parasitic infection in a subject or plant comprising administering to a subject a compound of formula (I) or formula (II) or a pharmaceutically acceptable salt thereof.

In preferred embodiments, the parasite is a helminth (worm), especially nematodes, trematodes and cestodes, such as *Haemonchus contortus, Trichinella spiralis, H. placei, Bursaphelenchus xylophilus, Ostertagia circumcincta, O. ostertagi, Mecistocirrus digitatus, Trychostrongylus axei, Trichuris trichiura, T. vulpis, T. campanula, T. suis, T. ovis, Bunostomum trigonocephalum, B. phleboyomum, Oesophagostomum columbianum, O. radiatum, Cooperia curticei, C. punctata, C. oncophora, C. pectinata, Strongyloides papillosus, Chabertia ovina, Ancylostoma duodenale, A. braziliense. A. tubaeforme, A. caninum, Ascaris lumbricoides, Enterobius vermicularis, E. gregorii, Ascaris lumbricoides, Paragonimus Westermani, Clonorchis sinensis, Fasciola hepatica, Taenia solium, T. saginata, Capillaria aerophila, Necator americanus*, species of the genus *Trichuris, Baylisascaris, Aphelenchoides, Meliodogyne, Heterodera, Globodera, Nacobbus, Pratylenchus, Ditylenchus, Xiphinema, Longidorus, Trichodorus, Nematodirus.*

In this embodiment, preferred compounds include 12-tigloyl-13-(2-methylbutanoyl)-6,7-epoxy-4,5,9,12,13,20-hexahydroxy-1-tigliaen-3-one (EBI-46), 12,13-di-(2-methylbutanoyl)-6,7-epoxy-4,5,9,12,13,20-hexahydroxy-1-tigliaen-3-one (EBI-47) and 12-(deca-2,4-dienoyl)-6,7-epoxy-4,5,9,12,13,20-hexahydroxy-1-tigliaen-3-one (EBI-61).

In yet another aspect of the invention, there is provided a method of treating or preventing a cell proliferative disorder in a subject comprising administering to a subject a compound of formula (I) or formula (II) or a pharmaceutically acceptable salt thereof.

In a preferred embodiment, the cell proliferative disorder is a cancer, especially where the cancer is selected from leukaemia, melanoma, prostate cancer, breast cancer, ovarian cancer, basal cell carcinoma, squamous cell carcinoma, fibrosarcoma, colon cancer, lung cancer, neoplasms and other solid tumour cancers. In one embodiment, the cell proliferative disorder is a dermatological neoplasm, particularly equine sarcoides.

In other embodiments, the cell proliferative disorder is a non-cancerous proliferative disorder. Examples of such non-cancerous proliferative disorders include dermatological disorders such as warts, keloids, psoriasis, proud flesh disorder and also reduction in scar tissue and cosmetic remodelling.

In preferred embodiments of the treatment or prevention of dermatological cell proliferative disorders, the therapy is preferably topical or administered intra-lesionally to provide a localised effect.

Without wishing to be bound by theory, the compounds of the invention are thought to bind to the $C_1$ region of PKC activating signalling pathways such as the MAP kinase pathway resulting in release of cytokines (Challacombe et al., J. Immunol., 2006, 177:8123-32; Cozzi et al., Cancer Res., 2006, 66:10083-91). This localised stimulation of inflammatory response prevents, reduces or removes unwanted cells thereby treating or preventing cell proliferative disorders. Accordingly, in another aspect of the invention, there is provided a method of stimulating a localised inflammatory response comprising administering to a subject a compound of formula (I) or formula (II) or a pharmaceutically acceptable salt.

If the compound of the invention is administered locally to treat a cell proliferative disorder, it may be administered at a higher dosage level than if administered systemically. For systemic administration to treat the subset of tumours and lymphoid neoplasms that are highly sensitive to growth inhibition in culture, a lower dose of compound is administered, for example, in the μg/kg dosage. Whereas, localised administration may be up to 1000 times greater, for example in the mg/kg level. For the drug class of PKC activators the mechanism of action at low systemic doses is likely to involve direct action on the tumour cells producing senescence (Cozzi et al., 2006) or apoptosis (Hampson et al., Blood, 2005, 106:1362-8); whereas at high, localised doses the host response, associated with a local inflammatory response, is also important (Challacombe et al., 2006)

In some instances, it is advantageous to administer the compounds of the invention together with an anti-inflammatory agent to reduce unwanted inflammatory responses. Examples of suitable anti-inflammatory agents such as ibuprofen, aspirin, pentoxifylline, dexamethasone, prednisolone, prednisone, cortisone, beclamethasone, fluticasone, hydrocortisone, methyl-prednisolone, triamcinolone, budesonide, betamethasone, naproxen, nabumetone and Cox-2 inhibitors such as celecoxib, rofecoxib and valdecoxib. The compounds of the invention may be administered simultaneously, separately or sequentially with the anti-inflammatory agent.

In this embodiment, preferred compounds include 12-tigloyl-13-(2-methylbutanoyl)-6,7-epoxy-4,5,9,12,13,20-hexahydroxy-1-tigliaen-3-one (EBI-46), 12,13-di-(2-methylbutanoyl)-6,7-epoxy-4,5,9,12,13,20-hexahydroxy-1-tigliaen-3-one (EBI-47), 12-(deca-2,4-dienoyl)-6,7-epoxy-4,5,9,12,13,20-hexahydroxy-1-tigliaen-3-one (EBI-61) and 12-(dodeca-2,4,6-trienoyl)-13-(2-methylbutanoyl)-6,7-epoxy-4,5,9,12,13,20-hexahydroxy-1-tigliaen-3-one (EBI-59).

In yet another embodiment of the present invention, there is provided a method of treating or preventing a protozoan infection in a subject comprising administering to a subject a compound of formula (I) or formula (II) or a pharmaceutically acceptable salt thereof.

In a preferred embodiment, the protozoan infection is selected from *Giardia* spp., *Trichomonas* spp., *African trypanosomiasis*, amoebic dysentery, babesiosis, balantidial dysentery, Chaga's disease, coccidiosis, malaria and toxoplasmosis, especially *Giardia* spp. and *Trichomonas* spp. infections.

In this embodiment, a preferred compound is 12,13-di-(2-methylbutanoyl)-6,7-epoxy-4,5,9,12,13,20-hexahydroxy-1-tigliaen-3-one (EBI-47).

In yet another aspect of the present invention, there is provided a use of a compound of formula (I) or formula (II) in the manufacture of a medicament for treating or preventing a bacterial infection, a parasitic infection, a protozoan infection or a cell proliferative disorder.

The term "subject" as used herein includes humans, primates, livestock animals (eg. sheep, pigs, cattle, horses, donkeys), laboratory test animals (eg. mice, rabbits, rats, guinea pigs), companion animals (eg. dogs, cats), birds (eg. chickens, ducks, geese, parrots, cockatoos, pigeons, finches, raptors, ratites, quail, canaries), captive wild animals (eg. foxes, kangaroos, deer) and reptiles (eg. lizards and snakes). Preferably, the mammal is human, a livestock animal, a companion animal or a laboratory test animal. Even more preferably, the mammal is a human, a livestock animal or a companion animal.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 μg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 μg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

In another aspect of the invention, the compounds of the invention are suitable for use as a pesticide. The invention therefore further provides a pesticidal composition comprising a compound of formula (I) or formula (II) or an agriculturally or pesticidally acceptable salt thereof and a pesticidally acceptable carrier.

The pesticidal composition is preferably an insecticidal composition and may be in the form of an emulsifiable concentrate, a flowable, a wettable powder, a soluble powder, a solution, an aerosol, a dust, a granule or a bait. A person skilled in the formulation of pesticidal compositions would be able to prepare such formulations.

Suitable carriers for pesticidal compositions include, but are not limited to, oils, especially petroleum oils, emulsifiers, solvents such as water or hydrocarbons, surfactants, aerosol spray components such as CFCs, talc or clay.

In yet another aspect of the invention, there is provided a method of controlling infestations of pests in a subject or an environment comprising applying a pesticidally effective amount of a compound of formula (I) or formula (II) to a subject or an environment infested with a pest.

The agricultural pest is preferably an insect, especially flies, beetles, grasshoppers, locusts, butterflies and moths and their larvae or nymphs, especially the flies (Diptera) such as true flies, fleas, ticks, lice, mosquitoes, gnats and midges.

In some embodiments, the pest infests plants. Examples of such pests include, but are not limited to, *Acyrthosiphon kondoi* (blue-green aphid), *Acyrthosiphon pisum* (pea aphid), *Agrotis* spp. (cutworm), *Agrypnus variabilis* (sugarcane wireworm), *Anoplognathus* spp. (christmas beetles), *Aphodius tasmaniae* (blackheaded pasture cockchafer), *Austroasca alfalfae* (lucerne leaf hopper), *Bathytricha truncate* (sugarcane and maize stemborer), *Bemisia tabaci* (whitefly), *Brachycaudus helichiysi* (leaf curl plum aphid), *Brevicoryne brassicae* (cabbage aphid), *Bruchophagus roddi* (lucerne seed wasp), *Bruchus pisorum* (pea weevil), *Biyobia* spp. (bryobia mite), *Clampa arietaria* (brown pasture looper), *Chortoicetes terminifera* (Australian plague locust), *Chrysodeitis angentifena* (tobacco looper), *Chrysodeitis eriosoma* (green looper), *Contarinia sorghicola* (sorghum midge), *Deroceras* spp. (slugs), *Diachrysia oricalcea* (soybean looper), *Etiella behrii* (lucerne seed-web moth), *Frankliniella schultzei* (tomato thrips), *Graphognathus leucoloma* (white fringed weevil), *Halotydeus destructor* (redlegged earth mite), *Hednota pedionoma* (pasture webworm), *Helicoverpa armigera* (corn earworm), *Helicoverpa punctigera* (native budworm), *Helix* spp. (snails), *Heteronychus arator* (African black beetle), *Leucania convecta* (common armyworm), *Lipaphis erysimi* (turnip aphid), *Listroderes difficilis* (vegetable weevil), *Melanacanthus scutellaris* (brown bean bug), *Merophyas divulsana* (lucerne leaf roller), *Myzus persicae* (green peach aphid), *Nala lividipes* (black field earwig), *Mythimna convector* (common armyworm), *Nezara viridula* (green vegetable bug), *Nysius vinitor* (rutherglen bug), *Nysius clevelandensis* (grey cluster bug), *Oncopera rufobrunnea* (underground grass grub), *Orondina* spp. (false wireworm), *Othnonius batesi* (black soil scarabs), *Penthaleus major* (blue oat mite), *Persectania ewingii* (southern armyworm), *Petrobia lateens* (brown wheat mite), *Pieris rapae* (cabbage white butterfly), *Piezodorus hybneri* (redbanded shield bug), *Plutella xylostella* (cabbage moth/diamondback moth), *Rhopalosiphum maidis* (corn aphid), *Sericesthis* spp. (small brownish cockchafers), *Sitona discoideus* (sitona weevil), *Sminthurus viridis* (lucerne flea), *Spodoptera exigua* (lesser armyworm), *Spodoptera letura* (cluster caterpillar *Spodoptera mauritia* (lawn armyworm), *Stomopteryx simplexella* (soybean moth), *Tetranychus ludeni* (bean spider mite), *Tetranychus urticae* (two spotted mite), *Therioaphis trifolii f. maculata* (spotted alfalfa aphid), *Thrips tabaci* (onion thrips), *Thrips imaginis* (plague thrips), *Zizina labradus* (grass blue butterfly), *Zygrita diva* (lucerne crown borer).

In other embodiments, the pests infest subjects and/or environments other than plants. Examples of such pests include, but are not limited to, lice, ants including *Camponotus* spp., *Lasius alienus, Acanthomyops interjectus, Monoinorium pharaonis, Solenopsis molesta, Tetramorium caepitum, Monomorium minimum, Prenolepis impairs, Formica exsectoides, Iridomyrmex pruinosus, Cremastogaster lineolata, Tapinoma sessile, Paratrechina longicornis*, cockroachs, mosquitos, bed bugs including *Leptoglassus occidentalis, Acrosternum hiare, Chlorochroa sayi, Podius maculiventris, Murgantia histrionica, Oncopeltus fasciatus, Nabis alternatus, Leptopterna dolabrata, Lygus lineolaris, Adelpocoris rapidus, Poecilocapsus lineatus, Orius insidiosus, Corythucha ciliata*, bees, wasps, black widow spider, booklice, boxelder bug, brown recluse spider, clothes moths including *Tineola* spp., *Tinea* spp., *Trichophaga* spp., carpet beetles, centipedes, clover mites, cluster and face flies, cigarette and drugstore beetles, crickets including *Acheta* spp., *Gryllus* spp., *Gryllus* spp., *Nemobius* spp., *Oecanthus* spp., *Ceuthophilus* spp., *Neocurtilla* spp., daddy-long-legs, domestic flies, drain flies, earwigs, European hornet, fleas including *Ctenocephalides felis, Ctenocephalides canis, Ctenocephalides* spp., *Nosopsyllusfasciatus, Nosopsyllus* spp., *Xenopsylla cheopis, Xenopsylla* spp., *Cediopsylla simplex, Cediopsylla* spp., fungus gnats, ground beetles, hide and larder beetles, horse/cattle/deer/pig flies, house dust mites including *Dermatophagoides farinae, Dermatophagoides pteronyssinus, Dermatophagoides* spp., mites including *Ornithonyssus sylviarum, Dermanyssus gallinae, Ornithonyssus bacoti, Liponyssoides sanuineus, Demodexfolliculorum, Sarcoptes scabiei hominis, Pyemotes tritici, Acarus siro, Tyrophagus putrescentiae, Dermatophagoides* sp., human lice, humbacked flies, Indian meal moth, millipedes, mud daubers, multicolored asian lady beetle, house borer, midges and crane flies, periodical and "dog-day" cicadas, powderpost beetles, roundheaded and flatheaded borers, pseudoscorpions, psyllids or jumping plant lice, spider beetles, sac spiders, sap beetles, termites, silverfish and firebrats, sowbugs and pillbugs, springtails, stinging hair caterpillars, tarantulas, vinegar flies, wasps and hornets, wharf borer, woods cockroach, yellowjacket wasps, fungus beetles, seed weevils, sawtoothed and merchant grain beetles, confused and red flour beetles, granery and rice weevils, indian meal moth, mealworms, drain flies, ticks including *Dermacentar* spp., *Ixodes* spp., *Rhipicenphalus* spp., carpenter bees, fleas, assassin bugs, human lice, chiggers, mystery bugs, european hornet, stinging hair caterpillars, black-legged tick, mayflies, black flies, horsehair worms, crickets, gypsy moths, grasshoppers, gnats, midges, locusts, mosquitoes including, *Aedes albopictus, Aedes Canadensis Aedes triseriatus, Aedes tivittatus, Aedes vexans, Aedes* spp., *Anopheles quadrimaculatus, Anopheles* spp., *Coquillettidia perturbans, Coquillettidia* spp., *Culex pipiens, Culex* spp.

An agriculturally effective amount may be determined by those skilled in the art using known methods and would typically range from 5 g to 500 g per hectare.

The compounds of the invention may be applied to any environment in which pests are present. For example, an environment in which agriculture is carried out, for example, the growing of crops, trees, and other plants of commercial importance. The agricultural environment includes not only the plant itself, but also the soil and area around the plants as they grow and also areas where parts of plants, for example, seeds, grains, leaves or fruit, may be stored. The environment may also be a household environment or industrial environment.

A "household environment" includes environments that are inhabited by humans or animals and may include indoor environments such as carpets, curtains, cupboards, bedding and the air inside a house. An "industrial environment" includes environments which are used for industrial purposes such as manufacture, storage or vending of products. Industrial environments include warehouses, manufacturing plants, shops, storage facilities and the like.

In this aspect, preferred compounds of formula (I) and formula (II) include 12,13-di-(2-methylbutanoyl)-6,7-epoxy-4,5,9,12,13,20-hexahydroxy-1-tigliaen-3-one (EBI-47), 12-(deca-2,4-dienoyl)-6,7-epoxy-4,5,9,12,13,20-hexahydroxy-1-tigliaen-3-one (EBI-61) and 12-(dodeca-2,4,6-trienoyl)-13-(2-methylbutanoyl)-6,7-epoxy-4,5,9,12,13,20-hexahydroxy-1-tigliaen-3-one (EBI-59).

The invention further provides use of a compound of formula (I) or formula (II) as an pesticide.

Accordingly, the compound of formula (I) or formula (II) may be formulated in an appropriate manner for delivery to subjects, crops, pastures, forests and other agricultural environments, or household or industrial environments, preferably for the alleviation and/or eradication of one or more insect pests.

DETAILED DESCRIPTION

Activity Screening

Figure 1:
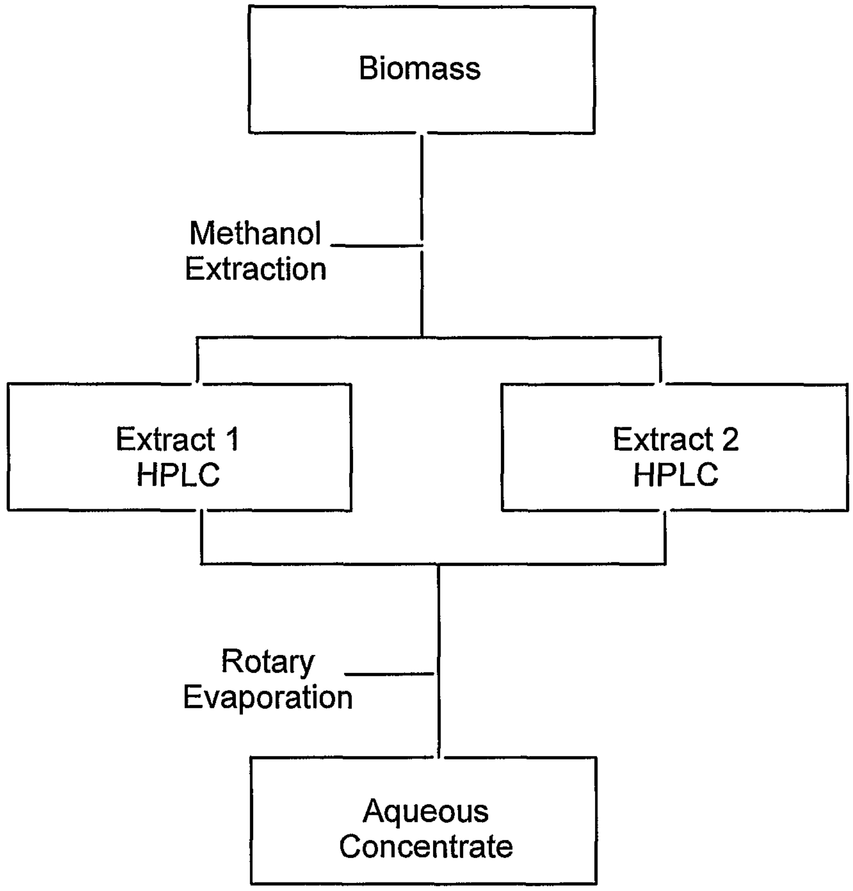
FIG. 1: Flowchart for initial solvent extraction of compounds of formula (I)

A solvent extraction sample from *Fontainea picrosperma* containing compounds of formula (I) and formula (II) were tested to determine therapeutical activity by screening in (A) a range of Microbial Screening Technologies (MST) bioassays, notably NemaTOX, ProTOX, MycoTOX, and CyTOX and DipteraTOX, and (B) a range of anticancer assays. For ease of description these bioassays will be described briefly prior to the extraction and chemical structure elucidation methodologies.

MST Bioassays Included:

NemaTOX (alternatively referred to herein as Ne) is an anthelmintic bioassay, applicable to all parasitic nematodes with free-living life cycle stages, and can be used as a screen to detect activity and define the species spectrum of compounds against parasitic nematodes and examine the impact of pre-existing resistance to other anthelmintic classes on potency. *Haemonchus contortus* was utilised for this assay.

The effect on larval development was determined in this assay by the method described by Gill et al. (1995) *Int. J. Parasitol.* 25: 463-470. Briefly, in this assay nematode eggs were applied to the surface of an agar matrix containing the test sample and allowed to develop through to the L3, infective stage (6 days). At this time the stage of larval development reached and any unusual features (deformity, paralysis, toxicity) were noted by microscopic examination.

ProTOX, (alternatively referred to herein as Bs) is an antibacterial bioassay, broadly applicable to most aerobic and anaerobic bacteria. The bioassay features a solid phase agar base into which the test compound has been incorporated together with a chromogen. As the bacteria multiply in the well, the chromogen is metabolised from blue in a two-step process to a colourless compound. Compounds with potent bactericidal activity inhibit bacterial metabolism of the chromogen while bacteriostatic compounds induce limited metabolism as indicated by an intermediate pink colour. ProTOX is broadly applicable to a range of gram-positive and gram-negative bacteria under aerobic and microaerophilic conditions. ProTOX assays were carried out using *Bacillus subtilis.*

Briefly, in ProTOX, the bacteria (24 hour broth) were applied to the surface of an agar matrix containing the test sample and allowed to grow for 48 hours. The assay was monitored at 24 and 48 hours and the active wells noted. Known antibiotics yield consistent colour transitions which are concentration and time dependent. These patterns provide an important guide to the early recognition of interesting characteristics. Bactericidal actives were assessed as having no colour change at both 24 and 48 hours while bacteriostatic actives were assessed as active at 24 hours but less potent or inactive at 48 hours.

MycoTOX (alternatively referred to herein as Tr) is a non-chromogenic bioassay used to detect activity against filamentous fungal pathogens of plants and animals. The bioassay features a solid phase agar base into which the test compound has been incorporated. As the growth patterns of filamentous fingi are readily apparent on the agar surface the extent of mycelial growth, sporulation (if relevant to the species under investigation) and colour changes with maturation are measured. Compounds with potent antifungal activity inhibit germination of fungal spores and provide a stark contrast to wells containing inactive compounds with the excessive fungal growth. Lower concentrations of such compounds, or compounds exhibiting a more fungistatic mode of action, show reductions in mycelial growth, extent of sporulation or reductions in other characteristic patterns of colony maturation.

MycoTOX, involves a fungus (spore suspension or mycelial fragments) being applied to the surface of an agar matrix containing the test chemical and allowed to grow for a period of up to a week (depending on species). The assay is monitored at two discrete times to identify key development phases in the life cycle (for example mycelial growth and extent of sporulation) and the active wells noted. The monitoring times are dependent on the fungal species under investigation.

The MycoTOX assays were carried out using *Trichophyton rubrum*. The MycoTOX test is alternatively referred to as Tr to indicate the use of *Trichophyton rubrum.*

CyTOX (alternatively referred to herein as Cy) is a microtitre plate bioassay use to identify potential antitumour actives. CyTOX is a chromogenic bioassay with broad application to a wide range of tumour and non-tumour cell lines. The colour transitions in CyTOX are proportional to cell metabolism and turnover and hence offer useful recognition patterns to support the diagnostic classification of actives within a framework of known cytotoxic and antitumour actives.

CyTOX features a liquid media into which the test compound has been incorporated together with a novel chromogen. As the cells grow and divide the chromogen is metabolised from purple in a single step process to a colourless metabolite. CyTOX was undertaken using NS1 murine myeloma cell line as a guide to mammalian cell toxicity.

Briefly, in CyTOX the cells were applied to the media containing the test chemical and allowed to grow for 72 hours. The assay was monitored at 24, 48 and 72 hours and the active wells identified.

DipteraTOX,

DipteraTOX is referred to herein as DipG, DipP and DipH. DipG represents no grazing of larva. DipP represents no pupae formation and Dip H represents no hatching of flies. A value of A in DipG, Dip P or Dip H represents very active and a value of P represents active. In DipteraTox the fly eggs were applied to the surface of an agar matrix containing 250 μg per mL of the test chemical and allowed to hatch, develop and pupate for a period up of two weeks. The assay was monitored at two discrete times to determine the extent of grazing of the agar matrix at Week 1 and the presence of adult flies at Week 2. Activity was scored qualitatively as active or inactive at Days 7 and 14 to denote failure to feed and failure to development to the adult stage, respectively.

TriTOX (alternatively referred to herein as Gi)

is a microtitre plate based chromogenic bioassay for the screening of anti-protozoan activity of pathogenic, anaerobic/microaerophilic protozoans for example *Giardia* spp. and *Trichomonas* spp. The bioassays are run under anaerobic conditions and features species specific chromogens. The minimum inhibitory concentrations (approximate LD99) are determined by the following method: stock solutions of the unknowns are serially diluted ½ to give 12 concentrations over a 2,048-fold range. Aliquots of each concentration(s) are applied to the wells of 96-well microtitre plates and diluted with media. Test substances are scored as active or inactive based on the chromogen colour change. The lowest concentration at which the compound is active is noted as the minimum inhibitory concentration (IC). Additionally, microscopic inspection is carried out to identify any patterns of morphological change that may be consistent with a type of toxicity and therefore mode of action. *Giardia* spp. was utilized for this assay.

Anticancer Assays Included:

SRB Assay for Inhibition of Growth of Cells Cultured as Monolayers

Briefly, a range of tumour cells including mouse melanoma, human melanoma, mouse squamous cell carcinoma, human breast, human colon, human leukemia and human lung and normal human cells including normal human fibroblasts were seeded at 2-5,000 per microtitre well (96-well plate) in 10% FCS-RPMI 1640 culture medium, treated, and allowed to grow until the controls were nearly confluent (5-6 days). The wells were then washed twice with PBS, fix with ethanol for a minimum of 5 minutes and washed with water. SRB solution (50 μL of 0.4% in 1% acetic acid) was added and left at room temperature for a minimum of 15 minutes. The plate was washed rapidly with tap water and then twice with 1% acetic acid. After addition of 100 μL/well of 10 mM Tris base (unbuffered, pH>9), plates were left for a minimum of 5 minutes, then the absorbance was read at 564 nm on the ELISA reader, with a 3 second prior shaking. After subtraction of a blank (wells with no cells, absorbance typically about 0.04), growth inhibition was calculated as % of the untreated control and plotted against dose.

QIMR Assay for Inhibition of Growth of Cells Cultured in Suspension

Briefly, a suspension of a range of tumour cells including mouse melanoma, human melanoma, mouse squamous cell carcinoma, human breast, human colon, human leukemia and human lung and normal human cells including normal human fibroblasts were seeded into round-bottom microtitre plates in 10% FCS-RPMI 1640 culture medium, treated and allowed to grow for 5-6 days. To measure cell growth, 20 μL of a combined MTS/PMS solution (Promega Cell ProliferationAssay Kit Cat#G5430) was added to each well of the 96 well assay plate. After 1-4 hours the plates were placed in the ELISA plate reader and the absorbance read at 490 nm. After subtraction of a blank (wells with no cells, absorbance typically about 0.4), growth inhibition was calculated as % of the untreated control and plotted against dose.

Topical Treatment of Tumours on Mice

Tumour cells were injected subcutaneously (2 million cells/site in 50 μL culture medium for LK2 cells, 0.5 million for B16) into 4 sites each on the flanks of nude mice (for LK2 cells) or C57BL/6 mice (B16 mouse melanoma cells). When tumours became visible (2-4 mm diameter) five to 10 days after injection of cells, 37 μg of EBI-46 in 25 μL of isopropanol gel was applied to each tumour site, each day for 3 days. Tumour size was measured with calipers at appropriate intervals.

Intralesional Injection at the Tumour Site on Mice

Squamous Cell Carcinoma (SCC) tumours were established by the same method as for topical treatment but were allowed to grow for 15 days before drug treatment. 7 μg EBI-46 in 20 μL saline was injected into each of 3 sides of the tumour. Tumour size was measured with calipers at appropriate intervals.

In order that the invention may be readily understood and put into practical effect, particular preferred embodiments will now be described by way of the following non-limiting examples.

EXAMPLE 1

Methods

Extraction

Biomass samples, including seeds, leaves and bark, from *Fontainea picrosperma* where collected and subject to the following extraction process. These samples and their subsequent fractions are referred in the below example as EB548.

Phase 1—Extraction

The biomass is generously covered with methanol and shaken (~2 L, overnight) followed by filtration to give the first extract. This process is repeated a second time (~2 L, ~5 hours) to generate the second extract. Each extract is examined by analytical HPLC and bioassayed (FIG. 1). The sequential methanol extracts are combined and the solvent removed by rotary evaporation to afford an aqueous concentrate.

Phase 2—Solvent Partition

Figure 2A:
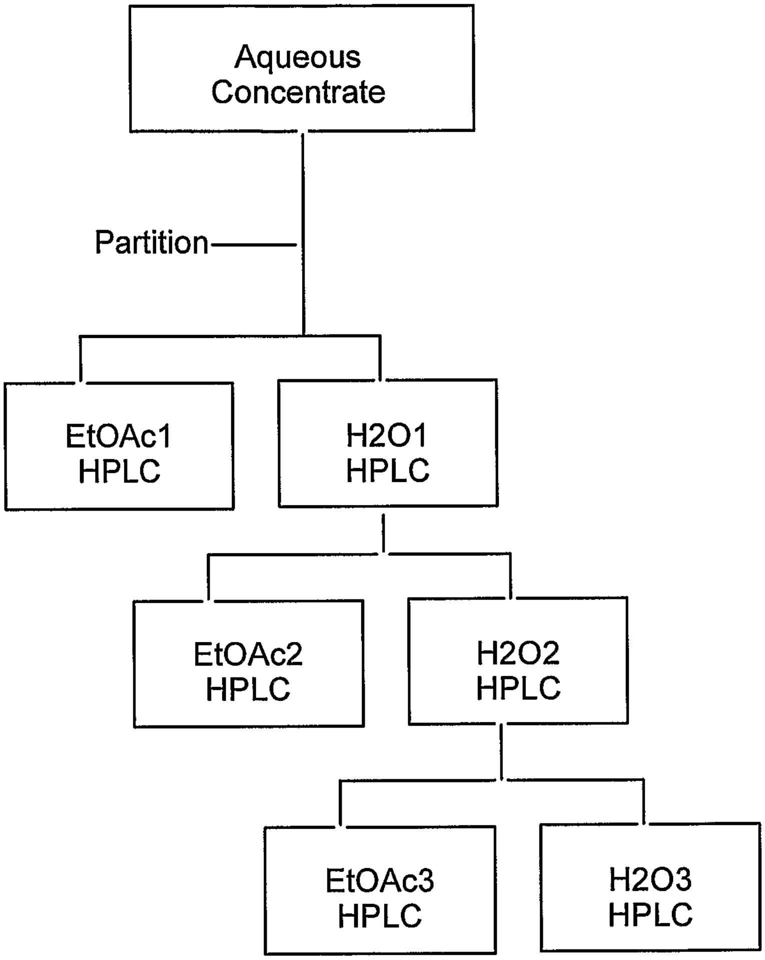
FIG. 2A: Flowchart showing the solvent partition for the aqueous concentrate obtained from the extraction shown in FIG. 1.

The aqueous concentrate from the extraction is diluted with water to 400 mL. The diluted sample (code 'Cr') is subsampled for HPLC and bioassay, then shaken with an equal volume of ethyl acetate (EtOAc) in a separatory funnel and the individual layers, EtOAc1 and H2O1, collected. Note, occasionally a precipitate would form that was insoluble in either layer. This precipitate was collected by filtration and dissolved in methanol (code 'Me'). The lower aqueous layer (H2O1) was twice more extracted with ethyl acetate to give EtOAc2 and EtOAc3 along with the remaining H2O3 layer. Subsamples of all layers are examined by analytical HPLC and bioassay (FIG. 2A).

Figure 2B:
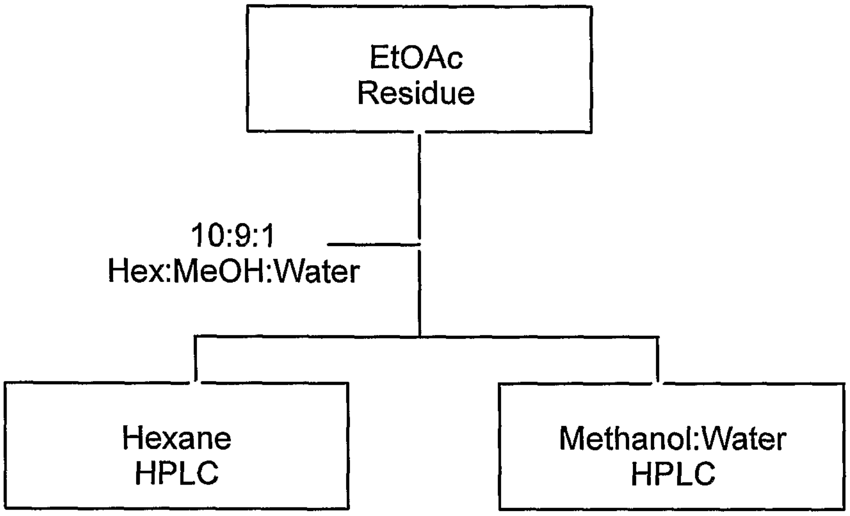
FIG. 2B: Flowchart showing the solvent partition for the ethyl acetate residue obtained from the extraction shown FIG. 1.

The sequential ethyl acetate extracts are pooled and the solvent removed by rotary evaporation to afford a residue that is weighed. On occasions, analytical HPLC indicated the EtOAc extract contained considerable amounts of extremely lipophilic (RT>9 minutes) material. To remove this material a 10:9:1-hexane:methanol:water partition was performed (FIG. 2B).

Phase 3—Preparative HPLC Fractionation

Figure 3:
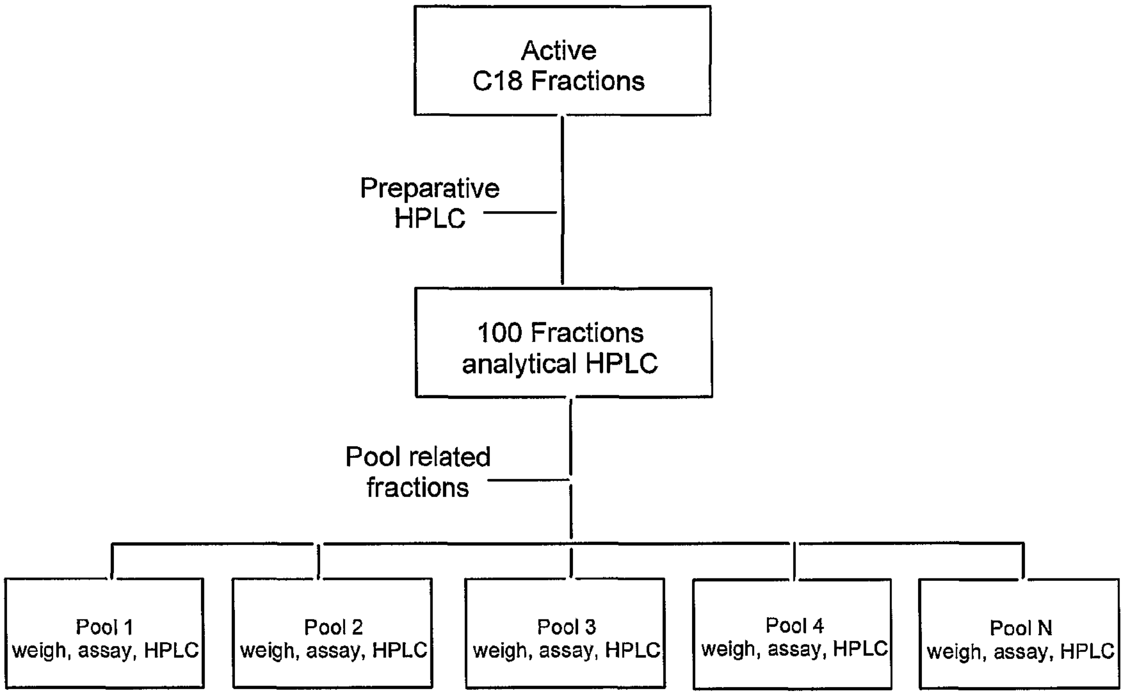
FIG. 3: Flowchart showing the steps in preparative HPLC chromatography.

The residue from the solvent partition is investigated by analytical HPLC to find optimum chromatographic conditions for separation of the metabolites present. Using these optimum conditions the residue (~2 g) is fractionated by preparative reverse phase HPLC (C18, single injection) into 100 fractions (FIG. 3). Subsamples of all 100 fractions are examined by analytical HPLC. After analysis of the HPLC traces, the 100 fractions are consolidated into 20 to 30 pooled fractions (pools), some of which may be >80% pure. These pooled fractions are weighed, bioassayed and examined by analytical HPLC.

Solvent Partition Summary for EB548

Biomass samples of *Fontainea picrosperma* under went extraction and solvent partitioning, using phase 1 and 2 described above. Table 1 summarises the amounts of extractable material obtained after solvent partitioning with ethyl acetate.

TABLE 1

Weights after Ethyl Acetate Partition of Extracts

| Sample | Weight[1] | EtOAc[2] | % Ext.[3] | HPLC Comment |
|---|---|---|---|---|
| EB548 | 318 | 68.4 | 21.5% | Excellent |

[1]Weight: Total sample weight in grams of plant material supplied and used for the study.
[2]EtOAc: Ethyl acetate extractables.
[3]% Ext.: Ethyl acetate extractables expressed as a percentage of the total sample weight.

Preparative HPLC

The preparative HPLC was carried out on a system consisting of two Shimadzu LC-8A Preparative Liquid Chromatographs with static mixer, Shimadzu SPD-M10AVP Diode Array Detector and Shimadzu SCL-10AVP System Controller. The column used was 50×100 mm (diameter×length) packed with C18 Platinum EPS (Alltech).

Approximately 2 grams of ethyl acetate extracted material was dissolved in dimethyl sulphoxide (4 mL) and subjected to preparative HPLC with typically conditions being 60 mL/min with gradient elution of 30% to 100% acetonitrile/water over 20 minutes followed by acetonitrile for 10 minutes. One hundred fractions (20 mL) were collected, evaporated under nitrogen, and then combined on the basis of HPLC analysis.

UV Analysis

UV spectra were acquired during HPLC with the Shimadzu SPD-M10AVP Diode Array Detector as mentioned above.

NMR Analysis

All NMR spectra were acquired in d6-dimethyl sulphoxide and referenced to the residual dimethyl sulphoxide signals. 1D NMR spectra, $^{1}H$ and $^{13}C$ [APT], were acquired at 300 and 75 MHz respectively on a Varian Gemini 300BB (Palo Alto Calif. USA) spectrometer. 2D NMR spectra, HSQC, HMBC, COSY and TOCSY, and a 1D NMR $^{1}H$ spectrum were acquired on a Bruker DRX600 (600 MHz) NMR spectrometer.

Analysis of NMR data was performed using ACD/SpecManager and ACD/Structure Elucidator, both version 6.0 from Advanced Chemistry Development, Inc. (Toronto, ON, Canada).

Electrospray Mass Sepctrometry Analysis (ES-MS)

All positive electrospray mass spectra were performed on a Finnigan/Mat TSQ7000 LCMS/MS (San Jose Calif. USA).

EXAMPLE 2

EB548: Extraction and Solvent Partition

Extraction and solvent partitioning of EB548 afforded 318 g of material. Each of the extraction and solvent partition layers were tested for bioactivity using the above bioassays. It can be seen from Table 2 that the extracts and ethyl acetate layers of the solvent partition all contain high CyTOX and NemaTOX activity.

TABLE 2

Activity of Extracts and Solvent Partitions.

| Sample | Ne Titre | Ne $LD_{99}$[4] | Bs Titre | Bs $LD_{99}$[4] | Tr Titre | Tr $LD_{99}$[4] | Cy Titre | Cy $LD_{99}$[4] |
|---|---|---|---|---|---|---|---|---|
| EB548.MG1.20-Ext1 | 64 | 120 | 8 | 990 | 0 | | 256 | 31 |
| EB548.MG1.20-Ext2 | 4 | 740 | 2 | 1500 | 1 | 2900 | 64 | 46 |
| EB548.MG1.28-EtOAc1 | 256 | 110 | 16 | 1800 | 2 | 14000 | 1024 | 28 |
| EB548.MG1.28-EtOAc2 | 4 | 180 | 1 | 730 | 1 | 730 | 32 | 23 |
| EB548.MG1.28-EtOAc3 | 0 | | 2 | 150 | 1 | 290 | 16 | 18 |
| EB548.MG1.28-H2O1 | 2 | 3300 | 0 | | 0 | | 8 | 810 |
| EB548.MG1.28-H2O2 | 2 | 3600 | 2 | 3600 | 0 | | 32 | 230 |
| EB548.MG1.28-H2O3 | 64 | 110 | 0 | | 4 | 1800 | 64 | 110 |

[4] $LD_{99}$ in μg/mL calculated as weight of chemical in last well with activity, however the real value may be lower as end point not attained.

The successive aqueous concentrated extracts were subjected to HPLC. The column used was 50×100 mm (diameter×length) packed with C18 Platinum EPS (Alltech). Approximately 2 grams of extracted material was dissolved in dimethyl sulfoxide (4 mL) and subjected to preparative HPLC with typical conditions being 60 mL/minute with gradient elution of 30% to 100% acetonitrile/water over 20 minutes followed by acetonitrile for 10 minutes.

For comparison purposes the first ethyl acetate partition and the third water layers were analysed by HPLC. There was little or no compounds of interest remaining in the third water layer of the third water/ethyl acetate solvent partition.

First Preparative HPLC Fractionation

In a manner similar to that described in Phase 3 above the EB548 ethyl acetate solvent partition samples where pooled and further worked up using preparative HPLC chromatograph.

The preparative HPLC was used to produce 100 fractions. These fractions were pooled depending on the relative concentration of compounds indicated in the preparative HPLC chromatograph.

The bioactivity of each fraction or pooled fraction resulting from the preparative HPLC was determined using the above bioassay method. The results are summarized below at Table 3.

TABLE 3

Activity of Preparative HPLC Pools.

| Sample | Weight[5] | Ne Titre | Ne $LD_{99}$[4] | Bs Titre | Bs $LD_{99}$[4] | Tr Titre | Tr $LD_{99}$[4] | Cy Titre | Cy $LD_{99}$[4] |
|---|---|---|---|---|---|---|---|---|---|
| EB548.LA3.139-1/15 | 53.2 | 0 | | 0 | | 0 | | 16 | 100 |
| EB548.LA3.139-16 | 3.4 | 0 | | 0 | | 0 | | 2 | 53 |
| EB548.LA3.139-17 | 0.5 | 0 | | 0 | | 0 | | 4 | 3.5 |
| EB548.LA3.139-18 | 0.8 | 0 | | 0 | | 0 | | 0 | |
| EB548.LA3.139-19 | 1.4 | 0 | | 0 | | 0 | | 2 | 22 |
| EB548.LA3.139-20 | 1.9 | 2 | 30 | 0 | | 0 | | 2 | 30 |
| EB548.LA3.139-21 | 2.8 | 0 | | 0 | | 0 | | 2 | 43 |
| EB548.LA3.139-22 | 47.3 | 32 | 46 | 4 | 370 | 4 | 370 | 64 | 23 |
| EB548.LA3.139-23 | 17.4 | 16 | 34 | 2 | 270 | 2 | 270 | 32 | 17 |
| EB548.LA3.139-24 | 16.0 | 32 | 16 | 4 | 130 | 1 | 500 | 16 | 31 |
| EB548.LA3.139-25 | 1.5 | 1 | 47 | 0 | | 0 | | 2 | 23 |
| EB548.LA3.139-26/28 | 19.8 | 64 | 10 | 8 | 78 | 8 | 78 | 64 | 10 |
| EB548.LA3.139-29 | 0.8 | 1 | 24 | 0 | | 0 | | 2 | 12 |

TABLE 3-continued

Activity of Preparative HPLC Pools.

| | | Ne | | Bs | | Tr | | Cy | |
|---|---|---|---|---|---|---|---|---|---|
| Sample | Weight[5] | Titre | $LD_{99}$[4] | Titre | $LD_{99}$[4] | Titre | $LD_{99}$[4] | Titre | $LD_{99}$[4] |
| EB548.LA3.139-30/31 | 1.9 | 1 | 58 | 0 | | 0 | | 8 | 7.2 |
| EB548.LA3.139-32 | 1.3 | 0 | | 0 | | 0 | | 4 | 10 |
| EB548.LA3.139-33/34 | 4.6 | 0 | | 1 | 140 | 0 | | 16 | 8.9 |
| EB548.LA3.139-35/36 | 19.7 | 0 | | 0 | | 1 | 620 | 64 | 10 |
| EB548.LA3.139-37 | 39.2 | 0 | | 1 | 1200 | 4 | 310 | 128 | 10 |
| EB548.LA3.139-38 | 43.8 | 0 | | 1 | 1400 | 4 | 340 | 128 | 11 |
| EB548.LA3.139-39/40 | 148.2 | 4 | 1200 | 8 | 580 | 16 | 290 | 128 | 36 |
| EB548.LA3.139-41/43 | 498.9 | 16 | 970 | 32 | 490 | 64 | 240 | 256 | 61 |
| EB548.LA3.139-44/45 | 9.0 | 0 | | 0 | | 0 | | 8 | 35 |
| EB548.LA3.139-46/47 | 33.8 | 0 | | 0 | | 0 | | 32 | 33 |
| EB548.LA3.139-48/50 | 221.3 | 0 | | 1 | 6900 | 2 | 3500 | 64 | 110 |
| EB548.LA3.139-51/53 | 221.2 | 2 | 3500 | 0 | | 64 | 110 | 1024 | 6.7 |
| EB548.LA3.139-54/55 | 9.2 | 0 | | 2 | 140 | 1 | 290 | 16 | 18 |
| EB548.LA3.139-56 | 24.3 | 0 | | 0 | | 1 | 760 | 16 | 47 |
| EB548.LA3.139-57 | 46.0 | 0 | | 0 | | 0 | | 64 | 22 |
| EB548.LA3.139-58/60 | 58.6 | 0 | | 0 | | 0 | | 32 | 57 |
| EB548.LA3.139-61/63 | 22.2 | 1 | 690 | 0 | | 0 | | 16 | 43 |
| EB548.LA3.139-64 | 25.5 | 1 | 800 | 0 | | 0 | | 32 | 25 |
| EB548.LA3.139-65 | 7.9 | 1 | 250 | 0 | | 0 | | 8 | 31 |
| EB548.LA3.139-66 | 4.9 | 2 | 77 | 0 | | 0 | | 16 | 10 |
| EB548.LA3.139-67 | 45.3 | 0 | | 0 | | 0 | | 4 | 350 |
| EB548.LA3.139-68/69 | 19.3 | 0 | | 0 | | 0 | | 8 | 75 |
| EB548.LA3.139-70/71 | 5.6 | 0 | | 0 | | 0 | | 8 | 22 |
| EB548.LA3.139-72 | 3.2 | 0 | | 0 | | 0 | | 0 | |
| EB548.LA3.139-73/75 | 24.8 | 0 | | 0 | | 0 | | 2 | 390 |
| EB548.LA3.139-76/78 | 3.1 | 0 | | 0 | | 0 | | 0 | |
| EB548.LA3.139-79 | 0.3 | 0 | | 0 | | 0 | | 0 | |
| EB548.LA3.139-80/89 | 2.0 | 0 | | 0 | | 0 | | 1 | 63 |
| EB548.LA3.139-90/100 | 8.0 | 0 | | 0 | | 0 | | 4 | 63 |

[4]$LD_{99}$ in µg/mL calculated as weight of chemical in last well with activity, however the real value may be lower as end point not affained.

[5]Weight in mg.

Second Preparative HPLC Fractionation

To prepare additional material a second preparative HPLC fraction was performed. The HPLC pools from the second preparative HPLC fraction did not require bioassay as the active bands were chosen based on the UV spectra from the first preparative HPLC.

In performing the second preparative HPLC fractionation it was discovered that of the major active bands, fractions EB548.LA3.139-22/24, -35/38, -41/43 and -51/53, the latter three showed substantial instability. This instability was observed upon nitrogen evaporation but not while in acetonitrile/water solution at room temperature or on vacuum evaporation. To avoid decomposition the equivalent four bands of active metabolites from the second preparative HPLC were individually back extracted in the ethyl acetate and evaporated under vacuum. Analytical HPLC of these samples confirmed minimal decomposition.

Due to overlap of Band 2 with Band 3 some of the Band 2 metabolites are in Band 3. The results of the second preparative fractionation are summarised in Table 4.

TABLE 4

Activity of Preparative HPLC Pools.

| Sample | Weight[5] | Comment |
|---|---|---|
| EB548.LA4.40-1/10 | 14.2 | |
| EB548.LA4.40-11/13 | 3.0 | |
| EB548.LA4.40-14 | 3.0 | |
| EB548.LA4.40-15/22 | 27.2 | |
| EB548.LA4.40-23/24 | 7.6 | |
| EB548.LA4.40-25/28 | 5.4 | |
| EB548.LA4.40-29 | 2.6 | |
| EB548.LA4.40-30/33 | 8.8 | |
| EB548.LA4.40-34/35 | 6.5 | |
| EB548.LA4.40-36/38 | 88.4 | Band 1 - equivalent to EB548.LA3.139-22, 23, 24 |
| EB548.LA4.40-39 | 2.7 | |
| EB548.LA4.40-40/41 | 29.4 | |
| EB548.LA4.40-42 | 1.5 | |
| EB548.LA4.40-43/44 | 2.1 | |
| EB548.LA4.40-45 | 1.6 | |
| EB548.LA4.40-46/47 | 27.1 | |
| EB548.LA4.40-48/53 | 6.8 | |
| EB548.LA4.40-54/56 | 4.4 | |
| EB548.LA4.40-57/59 | 8.7 | |
| EB548.LA4.40-60/61 | 11.1 | Band 2 equivalent to EB548.LA3.139-35/36, 37, 38 |
| EB548.LA4.40-62/66 | 402.6 | Band 3 equivalent to EB548.LA3.139-41/43 |
| EB548.LA4.40-67/73 | 599.3 | |
| EB548.LA4.40-74/77 | 25.4 | Band 4 equivalent to EB548.LA3.139-51/53 |
| EB548.LA4.40-78/79 | 262.1 | |
| EB548.LA4.40-80/82 | 328.1 | |
| EB548.LA4.40-83/90 | 42.2 | |
| EB548.LA4.40-91/100 | 189.2 | |

[5]Weight in mg.

EXAMPLE 3

Chemical Structural Elucidation

EBI-46

The pool of like material (fractions 22 to 24 and fractions 36 to 41, 80.7 mg and 120.5 mg respectively from the first and second gradient preparative HPLC runs, respectively) was dissolved in methanol and subjected to preparative HPLC (10 mL/min with isocratic elution of 55% water/acetonitrile over 30 minutes, through a 5 μm Phenomenex Luna C18 (2) 20×100 mm column).

Fractions 17 to 20 were combined, concentrated under vacuum, freeze dried and the resulting product was analysed by UV spectroscopy, HPLC analysis, ES-MS and NMR (Table 5). From the HPLC, ES-MS and NMR analysis it was determined that EB548.LA4.61-17/20 contained the following compound, referred to here as EBI-46, (12-tigloyl-13-(2-methylbutanoyl)-6,7-epoxy-4,5,9,2,13,20-hexahydroxy-1-tiglien-3 one):

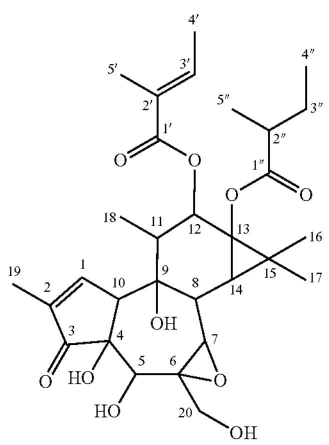

TABLE 5

NMR Data for EBi-46 in DMSO-$d_6$ at 75/600 MHz.

| No. | δ $^{13}C$ | δ $^{1}H$ | Multiplicity (J in Hz) |
|---|---|---|---|
| 1 | 161.2 | 7.60 | m |
| 2 | 132.7 | | |
| 3 | 207.2 | | |
| 4 | 73.1 | | |
| 5 | 67.8 | 3.94 | dd (6.5, 0.7) |
| 6 | 63.6 | | |
| 7 | 63.4 | 3.15 | s |
| 8 | 34.8 | 2.98 | d (6.6) |
| 9 | 76.6 | | |
| 10 | 49.0 | 4.07 | m |
| 11 | 45.5 | 1.85 | m |
| 12 | 77.3 | 5.35 | d (10.1) |
| 13 | 65.3 | | |
| 14 | 35.3 | 1.28 | d (6.6) |
| 15 | 26.6 | | |
| 16 | 23.4 | 1.14 | s |
| 17 | 17.0 | 1.20 | s |
| 18 | 14.5 | 0.68 | d (6.5) |
| 19 | 9.7 | 1.63 | dd (2.9, 1.3) |
| 20 | 62.3 | 3.82, 3.40 | dd (12.4, 5.8), dd (12.4, 6.7) |
| 1' | 166.9 | | |
| 2' | 128.1 | | |
| 3' | 137.1 | 6.72 | m |
| 4' | 14.2 | 1.75 | m |
| 5' | 12.1 | 1.74 | m |
| 1" | 177.3 | | |
| 2" | 40.4 | 2.30 | m |
| 3" | 25.8 | 1.57, 1.36 | m, m |
| 4" | 11.4 | 0.85 | t (7.5) |
| 5" | 16.1 | 1.04 | d (7.0) |
| 4-OH | | 5.49 | d (0.8) |
| 5-OH | | 5.17 | d (6.5) |
| 9-OH | | 5.29 | bs |
| 20-OH | | 4.45 | dd (6.7, 5.8) |

The bioassay results of Tables 6a, 6b and 6c clearly indicate that compound EBI-46 has efficacy as (A) a cytotoxic agent and therefore would be useful in the treatment and prophylaxis of cell proliferative diseases such as tumours, leukaemia, lymphoma and related disorders, (B) an antiparasitic and therefore would be useful in the treatment of infestation by a parasite, such as an ectoparasite and/or an endoparasites of humans and/or animals, and (C) an antibiotic and therefore would be useful in treatment or prophylaxis of an infection by bacteria of humans and/or animals.

TABLE 6a

| In vitro bioassay of EBI-46 | | | | | | | | | | |
|---|---|---|---|---|---|---|---|---|---|---|
| | | Ne | | Bs | | Tr | | Cy | | |
| Sample | Wt[5] | Titre | $LD_{99}$[4] | Titre | $LD_{99}$[4] | Titre | $LD_{99}$[4] | Titre | $LD_{99}$[4] |
| EB548.LA4.61-17/20 | 109.7 | 2 | 31 | 1 | 50 | 0 | — | 8 | 7.8 |

[4]$LD_{99}$ in μg/mL calculated as weight of chemical in last well with activity, however the real value may be lower as end point not attained.
[5]Wt is weight in mg.

TABLE 6b

| In vitro bioassays of EBI-46 | |
|---|---|
| Test cell line | Concentration of EBI-46 at which growth inhibition was observed |
| normal human fibroblasts (NFF) | None observed at 10 μg/mL |
| mouse melanoma B16 | =/<2 μg/mL |
| human melanoma MM96L | =/<2 μg/mL |
| human melanoma DO4 | <100 ng/mL |
| human melanoma MM127 | <100 ng/mL |
| Human melanoma SKMel-5 | <100 ng/mL |
| human leukemia K562 | <100 ng/mL |
| human leukemia U937 | <100 ng/mL |
| human breast CF-7 | <100 ng/mL |
| Mouse squamous cell carcinoma K-2 | <100 ng/mL |
| human colon Colo205 | <100 ng/mL |
| human lung A549 | <100 ng/mL |
| human lung H0P62 | <100 ng/mL |

TABLE 6c

| In vivo bioassays of EBI-46 | | |
|---|---|---|
| Cancer type | Mode of treatment | Results |
| Squamous cell carcinoma (SCC) | Topical treatment of LK2 mouse SCC in nude mice with a preparation of EBI-46 (37 ug/site) in isopropanol gel once a day for 3 days | Resulted in cure and healing without scarring of 3 out of 4 tumours; small area of growth on the 4$^{th}$ tumour possibly due to underdosing of this area. Area subsequently healed with minimal scarring. There were no signs of systemic toxicity or lung metastases on post mortem of experimental animals. |
| Squamous cell carcinoma (SCC) | Intralesional injection of 21 ug EBI-46 (3 × 20 ul injections of 7 ug each) into the periphery of two 15-day established tumours of LK-2 mouse SCC in a mouse | Resulted in significant reduction of tumour size. There were no signs of systemic toxicity or lung metastases on post mortem of experimental animals. |
| Melanoma | Topical treatment of B16 melanoma tumours in C57/B6 mice of 37 μg EBI-46 per site once a day for 3 days starting at day 5, | Resulted in significant inhibition of tumour growth. There were no signs of systemic toxicity or lung metastases on post mortem of experimental animals. |

EBI-47

In a similar manner to the elucidation of chemical structure outlined above, fractions 29 to 32 were combined, concentrated under vacuum, freeze-dried and the resulting product was analysed by UV spectroscopy, HPLC analysis, ES-MS and NMR (Table 7). From the HPLC, ES-MS and NMR analysis it was determined that EB548.LA4.61-29/32 contained the following compound, referred to herein as EBI-47 (12,13-di-(2-methylbutanoyl)-6,7-epoxy-4,5,9,12,13,20-hexahydroxy-tigliaen-3-one):

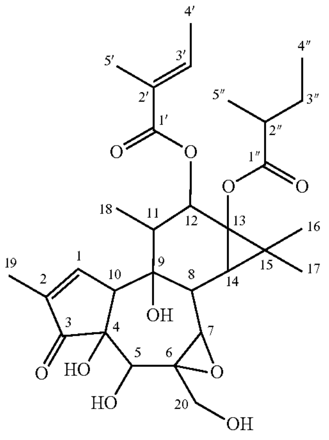

TABLE 7

| NMR Data for EBI-47 in DMSO-$d_6$ at 75/600 MHz. | | | |
|---|---|---|---|
| No. | δ $^{13}C$ | δ $^{1}H$ | Multiplicity (J in Hz) |
| 1 | 161.2 | 7.59 | m |
| 2 | 132.7 | | |
| 3 | 207.2 | | |
| 4 | 73.1 | | |
| 5 | 67.8 | 3.94 | d (6.5) |
| 6 | 63.6 | | |
| 7 | 63.3 | 3.15 | s |
| 8 | 34.8 | 2.98 | d (6.5) |
| 9 | 76.7 | | |
| 10 | 48.9 | 4.07 | m |
| 11 | 45.1 | 1.82 | m |
| 12 | 76.7 | 5.29 | d (10.3) |
| 13 | 65.2 | | |
| 14 | 35.2 | 1.30 | d (6.5) |
| 15 | 26.4 | | |
| 16 | 23.4 | 1.15 | s |

TABLE 7-continued

| NMR Data for EBI-47 in DMSO-$d_6$ at 75/600 MHz. | | | |
|---|---|---|---|
| No. | δ $^{13}C$ | δ $^{1}H$ | Multiplicity (J in Hz) |
| 17 | 16.9 | 1.16 | s |
| 18 | 14.5 | 0.70 | d (6.5) |
| 19 | 9.7 | 1.64 | dd (2.8, 1.0) |
| 20 | 62.3 | 3.82, 3.40 | dd (12.4, 5.8), dd (12.4, 6.9) |
| 1' | 175.2 | | |
| 2' | 40.9 | 2.32 | m |
| 3' | 26.2 | 1.55, 1.41 | m |
| 4' | 11.3 | 0.84 | t (7.4) |
| 5' | 16.6 | 1.06 | d (7.0) |
| 1" | 177.4 | | |
| 2" | 40.5 | 2.30 | m |
| 3" | 25.8 | 1.57, 1.37 | m |
| 4" | 11.3 | 0.85 | t (7.4) |
| 5" | 16.0 | 1.04 | d (7.0) |
| 4-OH | | 5.49 | s |
| 5-OH | | 5.17 | d (6.5) |
| 9-OH | | 5.30 | s |
| 20-OH | | 4.44 | t (6.3) |

The bio assay results of Tables 8a and 8b clearly indicate that compound EBI-47 has efficacy as a (A) a cytotoxic agent and therefore would be useful in the treatment and prophylaxis of a cell proliferative diseases such as a tumour, a leukaemia, a lymphoma and a related disorder, (B) an antiparasitic and therefore would be useful in the treatment of infestation by an antiparasitic such as an ectoparasite and/or an endoparasite of a human and/or an animal, (D) an antiprotozoal and therefore would be useful in treatment or prophylaxis of an infection by protozoa of humans and/or animals, and (C) an insecticide and therefore would be useful use in the eradication and/or growth inhibition of a an insect including a broad range of insect species.

TABLE 8a

| Bioassay of EBI-47 | | | | | | | |
|---|---|---|---|---|---|---|---|
| Sample | Wt | Ne Titre/ $LD_{99}$[4] | BS Titre/ $LD_{99}$[4] | Tr Titre/ $LD_{99}$[4] | Cy Titre/ $LD_{99}$[4] | DipH[4] | Gi Titre/ $LD_{99}$[4] |
| EB548.LA4.61-29/32 | 44.6 | 2/31 | 0/— | 0/— | 4/16 | P | 2/31 |

[4]$LD_{99}$ in μg/ml calculated as weight of chemical in last well with activity, however the real value may be lower as end point not attained.
[5]Wt is weight in mg.

TABLE 8b

| Bioassay of EBI-47 | |
|---|---|
| Test cell line | Concentration of EB548.LA4.61-29/32 At which growth inhibition was observed (μg/mL) |
| normal human fibroblasts (NFF) | None observed at 10 |
| human leukemia K562 | 0.1 |
| human melanoma MM418c5 | 0.03 |
| human prostate DU145 | 10 |
| human breast MCF-7 | 0.03 |

EBI-59

Approximately a quarter (100 mg) of pool of fractions 62 to 66, from the second gradient preparative HPLC run, was dissolved in methanol and subjected to preparative HPLC (10 mL/min with isocratic elution of 80% water/acetonitrile over 25 minutes, through a 5 μm Phenomenex Luna C18 (2)

20×100 mm column). Fraction 14 of the preparative HPLC was concentrated under vacuum, freeze-dried and the resulting product was analysed by UV spectroscopy, HPLC analysis, ES-MS and NMR (Table 9). From the HPLC, ES-MS and NMR analysis it was determined that EB548.LA4.85-14 contained the following compound, referred to herein as EBI-59 12-(dodeca-2,4,6-trienoyl)-13-(2-methylbutanoyl)-6,7-epoxy-4,5,9,12,13,20-hexahydroxy-1-tigliaen-3-one (EBI-59).

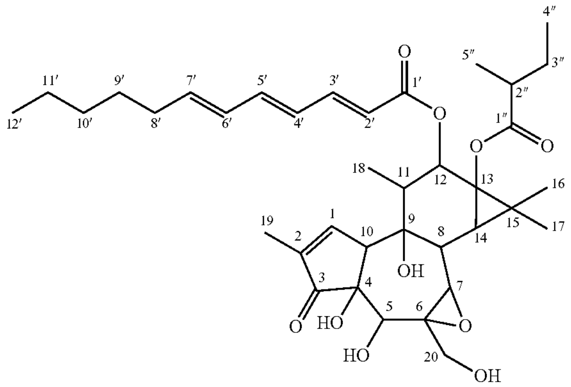

TABLE 9

| NMR Data for EBI-59 in DMSO-$d_6$ at 75/600 MHz. | | | |
|---|---|---|---|
| No. | δ $^{13}$C | δ $^{1}$H | Multiplicity (J in Hz) |
| 1 | 161.3 | 7.60 | s |
| 2 | 132.7 | | |
| 3 | 207.3 | | |
| 4 | 73.1 | | |
| 5 | 67.8 | 3.94 | d (6.4) |
| 6 | 63.6 | | |
| 7 | 63.4 | 3.15 | s |
| 8 | 34.8 | 2.98 | d (6.6) |
| 9 | 76.6 | | |
| 10 | 49.0 | 4.07 | m |
| 11 | 45.5 | 1.85 | m |
| 12 | 77.1 | 5.34 | m |
| 13 | 65.3 | | |
| 14 | 35.3 | 1.28 | m |
| 15 | 26.7 | | |
| 16 | 23.4 | 1.14 | s |
| 17 | 17.0 | 1.20 | s |
| 18 | 14.5 | 0.70 | d (6.4) |
| 19 | 9.7 | 1.64 | m |
| 20 | 62.3 | 3.82, 3.40 | dd (12.4, 5.6), dd (12.4, 6.7) |
| 1' | 166.0 | | |
| 2' | 119.9 | 5.89 | d (15.2) |
| 3' | 144.9 | 7.18 | dd (15.2, 11.3) |
| 4' | 127.8 | 6.33 | dd (14.9, 11.3) |
| 5' | 141.6 | 6.70 | d (14.9, 10.7) |
| 6' | 130.0 | 6.18 | dd (15.1, 10.7) |
| 7' | 140.6 | 5.98 | m |
| 8' | 32.3 | 2.11 | m |
| 9' | 28.1 | 1.36 | m |
| 10' | 30.8 | 1.24 | m |
| 11' | 21.9 | 1.25 | m |
| 12' | 13.9 | 0.84 | t (7.0) |
| 1" | 177.3 | | |
| 2" | 40.4 | 2.29 | m |
| 3" | 25.8 | 1.57, 1.35 | m, m |
| 4" | 11.4 | 0.85 | t (7.4) |
| 5" | 16.2 | 1.04 | d (7.0) |
| 4-OH | | 5.50 | s |
| 5-OH | | 5.16 | d (6.4) |
| 20-OH | | 4.45 | t (6.1) |

The bioassay results of Table 10 clearly indicate that compound EBI-59 has efficacy as (A) a cytotoxic agent and therefore would be useful in the treatment and prophylaxis of cell proliferative diseases such as tumours, leukaemia, lymphoma and related disorders, and (B) an insecticide and therefore would be useful use in the eradication and/or growth inhibition of an insect including a broad range of insect species.

TABLE 10

| Bioassay of EBI-59 | | | | | | |
|---|---|---|---|---|---|---|
| Sample | Wt[5] | Ne Titre/ $LD_{99}$[4] | Bs Titre/ $LD_{99}$[4] | Tr Titre/ $LD_{99}$[4] | Cy Titre/ $LD_{99}$[4] | DipP[4]/ DipH[4] |
| EB548.LA4.85-14 | 19.1 | 0/— | 0/— | 0/— | 16/3.9 | A/A |

[4]$LD_{99}$ in μg/mL calculated as weight of chemical in last well with activity, however the real value may be lower as end point not attained.
[5]Wt is weight in mg.

EBI-61

In a similar manner to the elucidation of chemical structure outlined above the pool of fractions 35 to 36 (19.7 mg), from the second gradient preparative HPLC run, was dissolved in methanol and subjected to preparative HPLC (10 mL/min with isocratic elution of 80% water/acetonitrile over 20 minutes, through a 5 μm Phenomenex Luna C18 (2) 20×100 mm column). Fraction 8 of the preparative HPLC run was concentrated under vacuum, freeze-dried and the resulting product was analysed by UV spectroscopy, HPLC analysis, ES-MS and NMR (Table 11). From the HPLC, ES-MS and NMR analysis it was determined that EB548.LA4.87-8 contained the following compound, referred to herein as EBI-61 12-(deca-2,4-dienoyl)-6,7-epoxy-4,5,9,12,13,20-hexahydroxy-1-tigliaen-3-one (EBI-61).

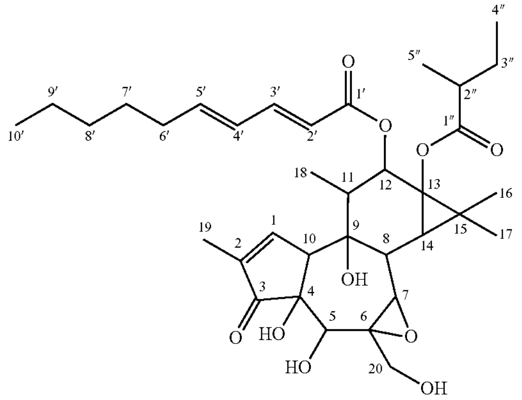

TABLE 11

| NMR Data for EBI-61 in DMSO-$d_6$ at 75/600 MHz. | | | |
|---|---|---|---|
| No. | δ $^{13}$C | δ $^{1}$H | Multiplicity (J in Hz) |
| 1 | 161.2 | 7.60 | s |
| 2 | 132.7 | | |
| 3 | 207.2 | | |
| 4 | 73.1 | | |
| 5 | 67.8 | 3.94 | d (6.5) |
| 6 | 63.6 | | |
| 7 | 63.4 | 3.16 | s |
| 8 | 34.9 | 2.96 | d (6.7) |

TABLE 11-continued

| NMR Data for EBI-61 in DMSO-$d_6$ at 75/600 MHz. | | | |
|---|---|---|---|
| No. | δ $^{13}C$ | δ $^1H$ | Multiplicity (J in Hz) |
| 9 | 76.6 | | |
| 10 | 49.1 | 4.07 | m |
| 11 | 45.6 | 1.84 | m |
| 12 | 77.4 | 5.34 | d (10.1) |
| 13 | 65.3 | | |
| 14 | 35.3 | 1.29 | m |
| 15 | 26.8 | | |
| 16 | 23.4 | 1.14 | s |
| 17 | 17.0 | 1.21 | s |
| 18 | 14.5 | 0.70 | d (6.4) |
| 19 | 9.7 | 1.64 | dd (2.8, 1.2) |
| 20 | 62.3 | 3.82, 3.40 | dd (12.4, 5.7), dd (12.4, 6.8) |
| 1' | 166.0 | | |
| 2' | 121.4 | 5.94 | d (15.2) |
| 3' | 139.0 | 7.45 | ddd (15.2, 11.7, 1.0) |
| 4' | 126.4 | 6.22 | m |
| 5' | 141.4 | 5.92 | m |
| 6' | 27.5 | 2.23 | m |
| 7' | 28.3 | 1.37 | m |
| 8' | 30.7 | 1.24 | m |
| 9' | 21.8 | 1.25 | m |
| 10' | 13.8 | 0.84 | t (7.2) |
| 1" | 177.2 | | |
| 2" | 40.4 | 2.30 | m |
| 3" | 25.8 | 1.57, 1.35 | m, m |
| 4" | 11.4 | 0.85 | t (7.3) |
| 5" | 16.2 | 1.04 | d (7.1) |

The bioassay results of Table 12 clearly indicate that compound EBI-61 has efficacy as a (A) a cytotoxic agent and therefore would be useful in the treatment and prophylaxis of a cell proliferative diseases such as a tumour, a leukaemia, a lymphoma and a related disorder, (B) an antiparasitic and therefore would be useful in the treatment of infestation by an antiparasite such as an ectoparasite and/or an endoparasite of a human and/or an animal, and (C) an insecticide and therefore would be useful use in the eradication and/or growth inhibition of an insect including a broad range of insect species.

TABLE 12

| Bioassay of EBI-61 | | | | | | |
|---|---|---|---|---|---|---|
| Sample | Wt[5] | Ne Titre/ $LD_{99}$[4] | Bs Titre/ $LD_{99}$[4] | Tr Titre/ $LD_{99}$[4] | Cy Titre/ $LD_{99}$[4] | DipP[4]/ DipH[4] |
| EB548.LA4.87-8 | 5.0 | 8/7.8 | 0/— | 0/— | 16/3.9 | P/P |

[4]$LD_{99}$ in μg/mL calculated as weight of chemical in last well with activity, however the real value may be lower as end point not attained.
[5]Wt is weight in mg.

12,13-di-(2-methylbutanoyl)-1,2-2H-1,2,6,7-diepoxy-6-carboxy-4,5,9,12,13-pentahydroxy-tigliaen-3-one

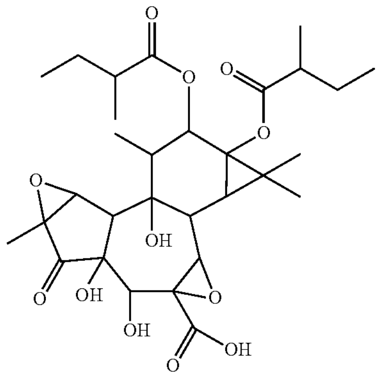

EBI-47 (1 mg) in 200 μL acetone was treated with 50 μL DMDO solution and stirred for 1 hour at 0° C. and 3 hours at room temperature to give 12,13-di-(2-methylbutanoyl)-1,2-2H-1,2,6,7-diepoxy-6-carboxy-4,5,9,12,13-pentahydroxy-tigliaen-3-one. MS (ESI) 617 (M+Na).

12,13-di-(2-methylbutanoyl)-5,20-di-acetoyl-4,5,9,12,13,20-hexahydroxy-tigliaen-3-one

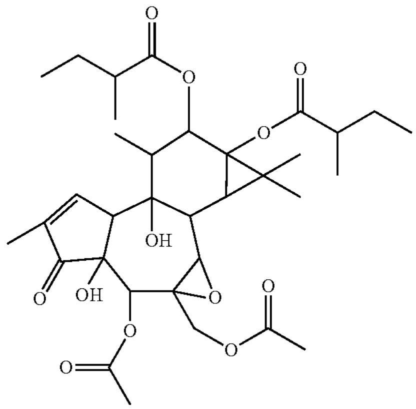

EBI-47 (1 mg) was treated with 400 μL acetic anhydride and pyridine solution (1:1) and stirred for 17 hours at room temperature to give 12,13-di-(2-methylbutanoyl)-5,20-di-acetoyl-4,5,9,12,13,20-hexahydroxy-tigliaen-3-one. MS (ESI) 671 (M+Na).

EXAMPLE 4

Mode of Activity

While not wanting to be bound by any one theory the compound EBI-46 is considered to be a protein kinase C activator on the basis of it's similar in vitro growth inhibition profiles to phorbol ester (TPA), selective inhibition of the growth of K562 leukemia, MCF-7 breast cancer, Colo-205 colon cancer and D04 and SKMel-5 melanoma at doses approximately 100-fold lower than for other human tumour cell lines and for normal human fibroblasts. In addition, scattering of MCF-7 and HT-29 colon tumour cells was observed, typical of PKC activators. A particular human melanoma cell line MM96L undergoes a characteristic change to bipolar morphology when treated with TPA or with EBI-46. Additionally, given their similarity in structure, EBI-47, EBI-59 and EBI-61 are also considered to be protein kinase C activators.

EXAMPLE 5

Cytotoxicity and Reduction in Tumours with EBI-46

Materials and Methods

Isolation of EBI-46 and Related Compounds

The raw plant material of *Fontainea picrosperma* (EB548 or EB610) was chopped, extracted with methanol, and partitioned between water and an organic solvent (diethyl ether or ethyl acetate). Pilot studies included HPLC and HPTLC activity-guided analysis, then optimization of the conditions for purification of bioactivity, and confirmation of stability. Fractionation of the bulk was conducted on silica gel 60 in petroleum spirit/acetone/methanol or in petroleum spirit/ethyl acetate/methanol, followed by HPLC. The latter involved reverse phase separation on a C18 Phenomenex Lunar 5 micron, 250×4.6 mm column in methanol-water.

The following gradient (Method EB.M, flow 2 mL/min) was used for the separation reported in Table 12.

TABLE 12

| | Time | | | | | | |
|---|---|---|---|---|---|---|---|
| | 0 | 15 | 39 | 40 | 45 | 46 | 55 |
| % MeOH | 70 | 80 | 84 | 100 | 100 | 70 | 70 |

Bioactivity Assays

The human tumour cell lines were: MCF-7 and T47D, breast cancer; DU145 and PC3, prostate cancer; C180-13S, ovarian cancer; MM96L, D04, SkMel5, melanoma; HT29, colon cancer. Neonatal foreskin fibroblasts (NFF) were used as normal control cells. Cells were cultured at 37° C. in 5% carbon dioxide/air, in RPMI 1640 medium containing 10% fetal calf serum.

For growth inhibition assays, cells (2000-5000/well) were seeded in 96-well plates in duplicate, treated with drug next day and allowed to grow for a further 5-6 days. The plates were then washed in PBS (phosphate buffered saline, pH 7.2), fixed with ethanol and stained by addition of 50 μL 0.4% SRB (sulforhodamine) in 1% acetic acid. The plate was left at room temperature for a minimum of 15 minutes, then washed rapidly with tap water and then twice with 1% acetic acid. After addition of 100 μL/well of 10 mM Tris base (unbuffered, pH>9), plates were left for a minimum of 5 minutes, then the absorbance was read at 564 nm on the ELISA reader, with a 3 second prior shaking. After subtraction of a blank (wells with no cells, typically about 0.04), growth inhibition was calculated as % of the untreated control and plotted against dose.

Animal experiments were conducted under Queensland Institute of Medical Research (QIMR) Animal Ethics Committee approvals. The B16 mouse melanoma model was obtained by injecting 0.5 million B16 mouse melanoma cells subcutaneously into each of the 2 flanks of a male C57BL/6 mouse. The human tumour xenografts were obtained by injecting 2 million of the respective tumour cell line into each of 4 sites on the flanks of male nude mice (BALB/c background). EBI-46 was applied: (a) topically by dilution of a concentrated solution in acetone into an isopropanol gel, once a day for 3 days; (b) intralesionally by injection into the tumour of drug dissolved in 25% propylene glycol-0.1 M saline, (c) systemically by injection intraperitoneally in 25% propylene glycol in 0.1 M saline. Tumour size was measured with electronic callipers in mm and converted to volume (cubic mm) using the formula:

$$\text{Tumour volume}=\text{length}\times\text{breadth}\times\text{breadth}/2.$$

Results

1. Purification of EBI-46 and Related Compounds

The organic extract was fractionated by chromatography on silica giving a fraction (548-35) containing a bioactive peak of high purity (RT: 25.131 minutes). Further purification by HPLC yielded >2 g of EBI-46 (RT: 25.262 minutes), from 2 kg of plant material.

2. Purity, Stability and Solubility

The bulk sample of EBI-46 was found to be >95% pure by UV and NMR, the limit of detection of the instruments.

Retention of bioactivity through extraction and chromatography steps implied that the structure was stable, and this has been confirmed to the extent that solutions of EBI-46 in ethanol retain bioactivity when held at 4° C. for 4 weeks. This was confirmed by an HPLC study of stability in the preferred delivery vehicle for intralesional injection (PEG 400 containing 10% ethanol) held at 37° C. The structure has no readily reactive groups which might otherwise confer instability.

Being a diterpene ester, EBI-46 is highly soluble in organic solvents including biocompatible solvents such as acetone, alcohols and PEG 400. It requires a small amount of such solvents to form aqueous solutions. Solubility tests have demonstrated 100% solubility at all 3 concentrations tested so far: 450 μg/mL in 90% water, 50 μg/mL in 99% water and 5 μg/mL in 99.9% water. Higher solubilities may well be achievable.

Note that EBI-46 is a potent drug and only small amounts are required. Thus for intralesional injection of EBI-46, the concentration was 400 μg/mL (and no water was required in this case).

3. Bioactivity Profile of EBI-46 and Related Compounds In Vitro: Arrest of Cell Growth The ability of the EB548 crude extract (Table 13), and purified EBI-46 (FIG. 4) to block the growth of cultured human tumour cell lines and a normal strain (human diploid fibroblasts) was tested in a clonogenic-type assay where many generations were allowed to elapse (5-6 days treatment) before measuring cell growth (Sulfurhodamine protein stain). Changes in morphology were also scored, and these were identical to those induced by the known protein kinase C (PKC) activator TPA (tetradecanoyl phorbol acetate), namely extreme bipolar morphology in the MM96L cell line and scattering of the MCF-7 cell clusters.

TABLE 13

Relative sensitivities of human cells to growth inhibition by EBI-46-rich crude extract (EB548)

| Cell | EB548 |
|---|---|
| Normal | |
| NFF | 700 |
| PBMC | 1.2 |
| Solid tumour | |
| A549 lung | <0.01 |
| D04 melanoma | 0.003 |

TABLE 13-continued

Relative sensitivities of human cells to growth inhibition by EBI-46-rich crude extract (EB548)

| Cell | EB548 |
|---|---|
| HOP62 lung | 0.002 |
| SKMel-28 melanoma | 200 |
| MM96L melanoma | 60 |
| MM127 melanoma | <0.001 |
| MCF-7 breast | 0.005 |
| Colo205 colon | <0.001 |
| HT29 colon | 200 |
| JAM ovarian | 100 |
| CI80-13S ovarian | 200 |
| Leukemia | |
| K562 | <0.001 |
| U937 | <0.01 |

Numbers represent the amount of crude extract required to produce 50% growth inhibition (IC50) of the cell line, relative to the JAM cell line (arbitrarily set to 100).

Figure 4:
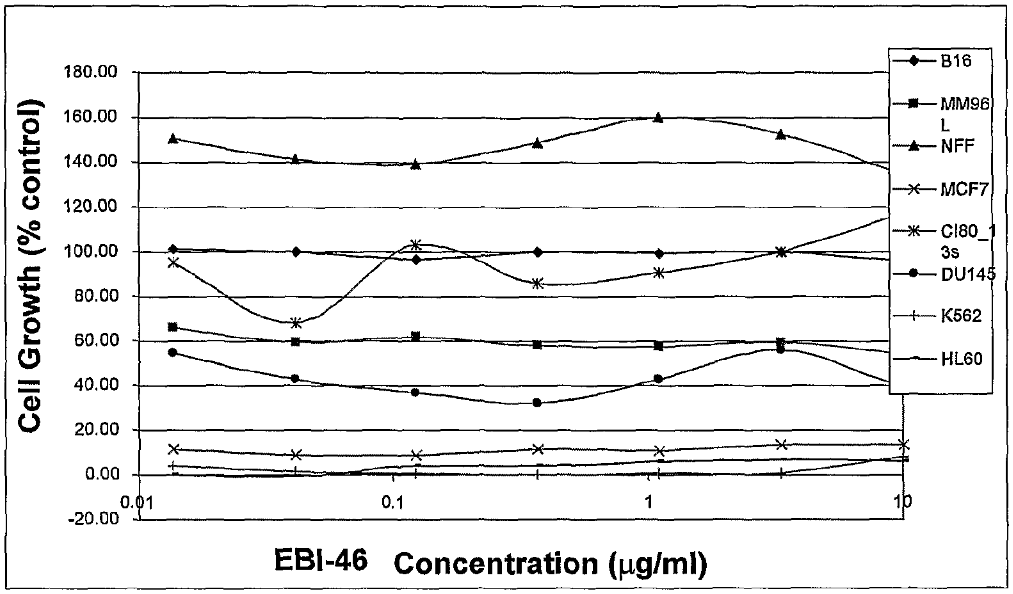
FIG. 4: Graphically represents the selective inhibition of cell growth in culture by EBI-46.

These results were confirmed for purified EBI-46 (FIG. 4)

The EBI-46/EB548-sensitive cell lines (K562, HL60, MCF7, Colo205, MM127, D04, U937) were also sensitive in a similar degree to growth inhibition by TPA (results not shown), at doses approximately 100-fold lower than for other human tumour cell lines and for normal human fibroblasts and PBMC (peripheral blood mononuclear cells). Further, EBI-46 induced the same bipolar morphology in MM96L and cell scattering of MCF-7 as TPA. Since such effects have previous been shown to be blocked by a PKC inhibitor, EBI-46 is considered to be a PKC activator.

Similar bioactivities were observed for EBI-47, EBI-61, EB610 p4011206 and EBI-59 as set out in Table 14.

TABLE 14

HPLC of *Fontainea picrosperma* isolate under following conditions:

| | |
|---|---|
| Column: | Phenomenex Luna 5u 250 × 4.60 mm C18 |
| Flow: | 2 mL/minute |
| Solvent system: | Methanol/water |

Gradient:

| | Time (min) | | | | | | |
|---|---|---|---|---|---|---|---|
| | 0 | 15 | 39 | 40 | 45 | 46 | 55 |
| % MeOH | 70 | 80 | 84 | 100 | 100 | 70 | 70 |

| Compound descriptor | Retention Time (min) | PKC activity* | Structure |
|---|---|---|---|
| EBI-46 | 23.2 | yes | EBI-46 |
| EBI-49 | 22.6# | yes | EBI-49 |
| EB610_EB_49.1 | 49.1 | yes | phorbol ring system*** |
| EB610_EB_26.6 | 26.6 | yes | EBI-47 |
| EB610_EB_32.3 | 32.3 | yes | phorbol ring system*** |
| EB610_EB_48.2 | 48.2 | yes | EBI-61 |
| EB610_p4_011206 | 46.4 | yes | phorbol ring system*** |
| EBI-59 | 17.8** | yes | EBI-59 |

*Activates PKC in cultured tumour cells as defined by scattering and growth inhibition of MCF7 breast cancer cells

**Run on a C18 Luna column, isocratic 80% acetonitrile-water

***As defined by NMR

#Run on a different HPLC column.

These compounds are therefore also considered to be PKC activators and of potential utility in the same indications as demonstrated for EBI-46 below.

4. Efficacy of EBI-46 in Treatment of Subcutaneous Tumours in Mice: Topical Application Topical application of EBI-46 in an isopropanol gel was carried out on the aggressive B16 mouse melanoma in its natural (syngeneic) host, C57BL/6 mice (0.5 million tumour cells injected per site).

The frequency (1 daily dose for 3 days only) and dose level for topical application of PKC activators was selected on the basis of in vitro activity on cell lines. The materials were dissolved in acetone and diluted into an isopropanol gel for topical application.

The aggressive and rapidly growing B16 mouse melanoma is recognised as a very stringent tumour model in which to test anticancer agents. Stringency was further increased by injecting at least 10× more tumour cells than the minimum required to form a tumour in the animal. A confounding factor in determining the efficacy of topical treatments was that some tumour cells escaped from the subcutaneous site at a early stage and became established in the underlying muscle where it is assumed that the drug and its associated dermal host response did not reach. Such tumours could be distinguished from subcutaneous tumours by their immobility when the skin was pulled around the body of the animal.

It was therefore highly significant that approximately 150 μg EBI-46/site gave a good response (4 mice and 4 controls, 2 sites/mouse), with one site apparently cured but the mouse had to be euthanased because the other site was growing. The inflammatory response was mild. There was no sign of systemic toxicity or lung metastases with any of the drugs.

Figure 5:
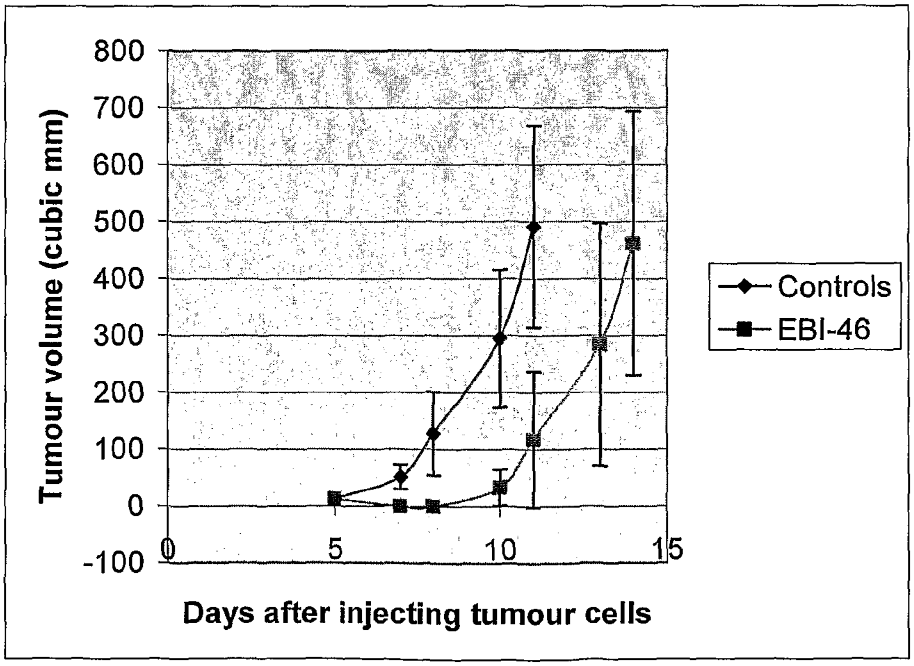
FIG. 5: Graphically represents the results of topical treatment of B16 tumours in C57/B6 mice with EBI-46 (once a day application for three days starting from day 5)

The regrowth of tumour cells after 10 days was not surprising, given the stringency of the model (FIG. 5) and the somewhat arbitrary choice of dose and regimen.

Figure 6:
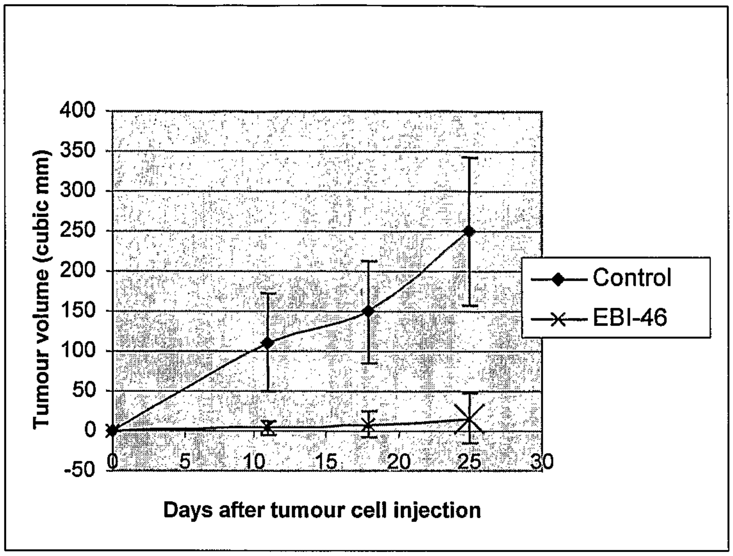
FIG. 6: Graphically represents the results of topical treatment of LK2 mouse SCC in nude mice.

The above was repeated using the UVB-induced mouse squamous cell carcinoma (SCC) grown on nude mice (FIG. 6) and treated with partially—purified EBI-46. This more realistic model for skin cancers showed an extremely high response rate which was maintained over a long period.

Again, an excellent result was obtained, with relapses occurring after 6 weeks due primarily to outgrowth of tumours from the underlying muscle, presumably due to being out of reach of the topical drug.

Figure 7:
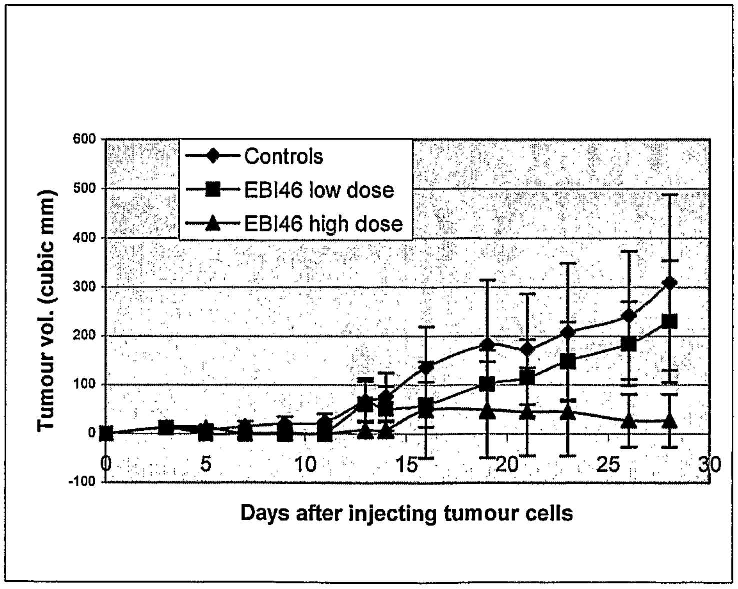
FIG. 7: Graphically represents the inhibition of growth of LKC SSC tumours by topical application of EBI-46.

The most recent experiment with topical application used 2 different doses of EBI-46 (FIG. 7). The low dose was 100 μg/site and the high dose was 350 μg/site/treatment.

This experiment gave an excellent result at 350 μg EBI-46/site, and showed that it was important to achieve a certain dose level to achieve efficacy.

5. Efficacy of EBI-46 in Treatment of Subcutaneous Tumours in Mice: Intralesional Injection A pilot study was conducted on 6 mm×6 mm LK-2 tumours established in nude mice. Approximately 50 μL of a solution of EB548 fractions (approximately 20 μg EBI-46 in the EB548-35 fraction) in saline containing 20% acetone were injected in 3 sites around the periphery of each lesion. This was only done once.

Figure 8:
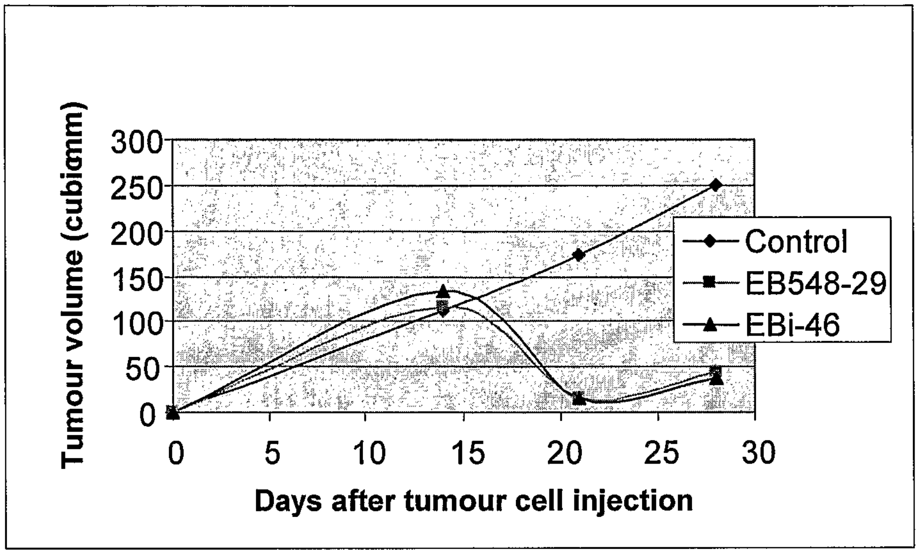
FIG. 8: Graphically represents the effect of injected EBI-46 on LK-2 SCC tumours.

The result showed rapid ablation of visible tumours, (FIG. 8) and an inflammatory response at the site of injection. Tumour growth eventually recovered, presumably due to non-optimal delivery.

The above procedure was then modified by using PEG 400 containing 10% ethanol as the vehicle. EBI-46 is freely soluble in this mixture and the increased viscosity served to restrict delivery of drug to the tumour site.

With PEG 400 delivery, 10 μg EBI-46 in 25 μL solution was injected (29 gauge) with a 0.5 mL insulin needle into a 7 mm×7 mm tumour, highly visible on the left flank of a nude mouse.

By 16 hours, a marked inflamed area had developed and the tumour lump had largely gone. A small area of normal skin on the ridge of the back was accidentally treated topically with the preparation, and developed a mild inflammatory response.

Seven days later, the tumour site was still flat and a scab had formed. The normal treated skin on the ridge of the back also formed a scab. This mouse remained tumour-free for over 9 months and was finally euthanased due to an unrelated condition (swollen penis).

In addition to the advantage of viscosity for localization of drug, PEG 400 gave fewer problems with leaking out after withdrawal of the needle. PEG 400 alone had no effect when injected into an LK2 tumour on another mouse.

A second mouse model was tested in a pilot study, involving an 8 mm diameter human nasopharyngeal tumour implanted and growing subcutaneously on the neck of a SCID-NOD mouse. Up to 3 injections of EBI-46 (total of 25 μg in 75 μL 25% propylene glycol-saline) were made into the NPC tumours of 2 mice. The scab sloughed off the treated site in one mouse, with no sign of residual tumour. Growth of the tumour in the second mouse was delayed but not ablated.

Systemic Administration of EBI-46

A variety of reports using cultured cells suggest that PKC activators may have potential for the treatment of lymphoid neoplasms. The murine B-cell lymphoma line A20 was used as an experimental model because it has been reported to grow well in mice and closely models the human situation.

SCID-NOD mice (BALB/c background) were shaved and 10E7 A20 cells injected subcutaneously (2 sites per mouse). The tumours tended to grow in a flat, diffuse manner and became raised and measurable at the 10E7 sites only after about 15 days. One mouse with 10E7 tumours was then injected intraperitoneally from day 18 with a total of 5 doses of 20-25 μg EBI-46 in 25% propylene glycol-saline. The solution was stable for weeks at 4° C., and there was no sign of insolubility at this concentration (250 μg/mL).

The results suggest that tumour growth in the injected mouse was strongly inhibited by EBI-46, compared with an untreated 10E7 mouse. Growth increased when the treatment stopped and the mouse was euthanased at 27 days.

Delivery Vehicles for EBI-46

Consideration of the structure and stability of EBI-46 leads to the use of protic solvents that are biocompatible. Benzyl alcohol and Cremaphor would be possibilities but have not been tested. PEG 400 was chosen because of its common usage, but similar solvents could well be suitable; and the use of larger needles would obviate the need to dilute slightly with ethanol. None of the above materials were deliberately sterilized, despite being used in the immunocompromised nude mice.

Safety Issues

The operator, as with any potent drug, should wear personal protection (gloves, coat/gown, eye protection). EBI-46 can cause inflammation of skin. It can be deactivated with sodium carbonate solution.

The animals have shown no weight loss, signs of distress or side effects. Internal organs appeared to be normal on dissection but no histology or formal toxicology has been done.

Discussion

EBI-46 is solvent extractable from EB548 material and although other compounds with similar activity are present, EBI-46 travels in an uncluttered region of the chromatogram and therefore is relatively easy to purify. The same bioactivities were obtained from the crude extract through to the purified structure. Properties relevant to its potential use as a pharmaceutical have so far been favourable: availability, purity, stability and solubility in delivery vehicle.

The cell growth inhibition profile revealed EBI-46 to be a PKC activator, showing very high selectivity for a subset of solid tumour and leukemia cell lines, compared with normal cells and some other tumour cell lines. Local application such as topical cream or intralesional injection into lesions is likely to clear these sites because of a combination of direct killing (high local dose) and elimination of peripheral tumour cells by the host's innate immune response as evidenced by the early inflammatory reaction at the site of application.

Intralesional injection required less drug than topical application, and only one treatment, to obtain a significant response. If relapse occurs, for example on one side of the original lesion, repeated injections would be possible. Injection also provides a more positive delivery than relying on topical application on sites of different skin thickness.

It is important to note that efficacy of local treatment does not require the target tumour to be intrinsically sensitive to EBI-46. The aggressive B16 mouse melanoma cells for example are quite resistant in culture but respond to the drug topically in the mouse. Presumably, the vigorous host response is a major factor. This C57BL/6 strain is very different from the BALB/c background of the nude mouse, indicating that neither strain differences nor lack of adequate T-cell immunity inhibit the efficacy of EBI-46.

The ability of local treatment with EBI-46 to work in species other than mice remains to be evaluated. Mouse skin is very thin (half the thickness of human skin), thus making intralesional injection more attractive. PEG 400 was chosen as a vehicle because it is used extensively for drug delivery and because its viscosity (lowered slightly with 10% ethanol to achieve injectability) may limit spreading away to far from the injection site.

Note also that EBI-46 causes an inflammatory response in normal skin. There are anecdotal reports of various plant saps being used to treat warts. This raises the possibility of using EBI-46 to ablate keloid scars, psoriasis, warts, proud flesh and other non-malignant conditions of the skin.

Local treatment may find significant application beyond skin lesions. It may be feasible to locally treat, by injection or suitably-formulated topical preparations, life-threatening tumours such as those of the oral cavity, esophagus and bowel. This could be carried out in conjunction with physical or pharmacological means of limiting escape of the drug into the circulation.

Throughout this specification, unless the context requires otherwise, the word "comprises", and variations such as "comprise" or "comprising", will be understood to imply the inclusion of a stated integer or group of integers or steps but not to the exclusion of any other integer or group of integers.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

The claims defining the invention are as follows:

1. A compound of formula (II):

(II)

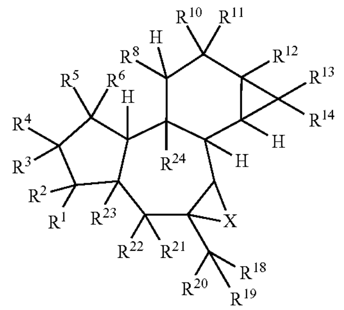

wherein:

X is —O—;

$R^1$ and $R^2$ are each independently hydrogen, —OH, —OC$_1$-C$_{10}$ alkyl, —OC$_2$-C$_{10}$ alkenyl, —OC$_2$-C$_{10}$ alkynyl, —Ocycloalkyl, —OC(O)C$_1$-C$_{10}$ alkyl, —OC(O)C$_2$-C$_{10}$ alkenyl, —OC(O)C$_2$-C$_{10}$ alkynyl, —OC(O)cycloalkyl, —OC(O)NHC$_1$-C$_{10}$ alkyl, —OC(O)NHC$_2$-C$_{10}$ alkenyl, —OC(O)NHC$_2$-C$_{10}$ alkynyl, —OC(O)NHcycloalkyl, —OC(O)NHaryl, —OC(S)NHC$_1$-C$_{10}$ alkyl, —OC(S)NHC$_2$-C$_{10}$ alkenyl, —OC(S)NHC$_2$-C$_{10}$ alkynyl, —OC(S)NHcycloalkyl, or —OC(S)NHaryl, or $R^1$ and $R^2$ taken together are ═O, ═S, ═NH or ═N(C$_1$-C$_6$ alkyl);

$R^3$ is hydrogen, —C$_1$-C$_{10}$ alkyl, —C$_2$-C$_{10}$ alkenyl or —C$_2$-C$_{10}$ alkynyl;

$R^4$ and $R^5$ are each independently hydrogen, —C$_1$-C$_{10}$ alkyl, —C$_2$-C$_{10}$ alkenyl, —C$_2$-C$_{10}$ alkynyl, —OH, —OC$_1$-C$_{10}$ alkyl, —OC$_2$-C$_{10}$ alkenyl, —OC$_2$-C$_{10}$ alkynyl, —Ocycloalkyl, —OC(O)C$_1$-C$_{10}$ alkyl, —OC(O)C$_2$-C$_{10}$ alkenyl, —OC(O)C$_2$-C$_{10}$ alkynyl, —OC(O)cycloalkyl, —OC(O)aryl, —OC(O)NHC$_1$-C$_{10}$ alkyl, —OC(O)NHC$_2$-C$_{10}$ alkenyl, —OC(O)NHC$_2$-C$_{10}$ alkynyl, —OC(O)NHcycloalkyl, —OC(O)NHaryl, —OC(S)NHC$_1$-C$_{10}$ alkyl, —OC(S)NHC$_2$-C$_{10}$ alkenyl, —OC(S)NHC$_2$-C$_{10}$ alkynyl, —OC(S)NHcycloalkyl, —OC(S)NHaryl, F, Cl, Br, I, —CN, —NO$_2$ or N(R$^{25}$)$_2$, or $R^4$ and $R^5$ taken together form a double bond or are —O—, —S—, —NR$^{25}$— or —CR$^{26}$R$^{27}$—;

$R^6$ is hydrogen, —C$_1$-C$_{10}$ alkyl, —C$_2$-C$_{10}$ alkenyl or —C$_2$-C$_{10}$ alkynyl;

$R^8$ is hydrogen, —C$_1$-C$_{10}$ alkyl, —C$_2$-C$_{10}$ alkenyl or —C$_2$-C$_{10}$ alkynyl;

$R^{10}$ is hydrogen, —C$_1$-C$_{10}$ alkyl, —C$_2$-C$_{10}$ alkenyl or —C$_2$-C$_{10}$ alkynyl;

$R^{11}$ is —OH, —OC$_1$-C$_{20}$ alkyl, —OC$_2$-C$_{20}$ alkenyl, —OC$_2$-C$_{20}$ alkynyl, —Ocycloalkyl, —OC(O)C$_2$-C$_{20}$ alkyl, —OC(O)C$_2$-C$_{20}$ alkenyl, —OC(O)C$_2$-C$_{20}$ alkynyl, —OC(O)cycloalkyl, —OC(O)aryl, —OC(O)NHC$_1$-C$_{20}$ alkyl, —OC(O)NHC$_2$-C$_{20}$ alkenyl, —OC(O)NHC$_2$-C$_{20}$ alkynyl, —OC(O)NHcycloalkyl, —OC(O)NHaryl, —OC(S)NHC$_1$-C$_{20}$ alkyl, —OC(S)NHC$_2$-C$_{20}$ alkenyl, —OC(S)NHC$_2$-C$_{20}$ alkynyl, —OC(S)NHcycloalkyl, or —OC(S)NHaryl, or $R^{10}$ and $R^{11}$ taken together form a carbonyl group (═O);

$R^{12}$ is —OH, —OC$_1$-C$_{20}$ alkyl, —OC$_2$-C$_{20}$ alkenyl, —OC$_2$-C$_{20}$ alkynyl, —Ocycloalkyl, —OC(O)C$_1$-C$_{20}$ alkyl, —OC(O)C$_2$-C$_{20}$ alkenyl, —OC(O)C$_2$-C$_{20}$ alkynyl, —OC(O)cycloalkyl, —OC(O)aryl, —OC(O)NHC$_1$-C$_{20}$ alkyl, —OC(O)NHC$_2$-C$_{20}$ alkenyl, —OC(O)NHC$_2$-C$_{20}$ alkynyl, —OC(O)NHcycloalkyl, —OC(O)NHaryl, —OC(S)NHC$_1$-C$_{20}$ alkyl, —OC(S)NHC$_2$-C$_{20}$ alkenyl, —OC(S)NHC$_2$-C$_{20}$ alkynyl, —OC(S)NHcycloalkyl, or —OC(S)NHaryl;

$R^{13}$ and $R^{14}$ are each independently hydrogen or —C$_1$-C$_{10}$ alkyl;

$R^{18}$ is C$_1$-C$_{20}$ alkyl, —C$_2$-C$_{20}$ alkenyl, —C$_2$-C$_{20}$ alkynyl, —OH, —OC$_1$-C$_{20}$ alkyl, —OC$_2$-C$_{20}$ alkenyl, —OC$_2$-C$_{20}$ alkynyl, —Ocycloalkyl, —OC(O)C$_1$-C$_{20}$ alkyl, —OC(O)C$_2$-C$_{20}$ alkenyl, —OC(O)C$_2$-C$_{20}$ alkynyl, —OC(O)cycloalkyl, —OC(O)aryl, —NHC$_1$-C$_{20}$ alkyl, —NHC$_2$-C$_{20}$ alkenyl, —NHC$_2$-C$_{20}$ alkynyl, —NHcycloalkyl, —NHaryl, —OC(O)NHC$_1$-C$_{20}$ alkyl, —OC(O)NHC$_2$-C$_{20}$ alkenyl, —OC(O)NHC$_2$-C$_{20}$ alkynyl, —OC(O)NHcycloalkyl, —OC(O)NHaryl, —OC(S)NHC$_1$-C$_{20}$ alkyl, —OC(S)NHC$_2$-C$_{20}$ alkenyl, —OC(S)NHC$_2$-C$_{20}$ alkynyl, —OC(S)NHcycloalkyl, or —OC(S)NHaryl;

$R^{19}$ and $R^{20}$ are each independently hydrogen, —C$_1$-C$_6$ alkyl, —C$_2$-C$_6$ alkenyl, —C$_2$-C$_{20}$ alkynyl, —OH, —OC$_1$-C$_6$ alkyl, —OC$_2$-C$_6$ alkenyl, —OC$_2$-C$_6$ alkynyl, —Ocycloalkyl, —OC(O)C$_1$-C$_6$ alkyl, —OC(O)C$_2$-C$_6$ alkenyl, —OC(O)C$_2$-C$_6$ alkynyl, —OC(O)cycloalkyl, or —OC(O)aryl, or $R^{19}$ and $R^{20}$ taken together form a carbonyl or thiocarbonyl group;

$R^{21}$ is hydrogen, —C$_1$-C$_{10}$ alkyl, —C$_2$-C$_{10}$ alkenyl or —C$_2$-C$_{10}$ alkynyl;

$R^{22}$ is —OH, —OC$_1$-C$_{20}$ alkyl, —OC$_2$-C$_{20}$ alkenyl, —OC$_2$-C$_{20}$ alkynyl, —Ocycloalkyl, —OC(O)C$_1$-C$_{20}$ alkyl, —OC(O)C$_2$-C$_{20}$ alkenyl, —OC(O)C$_2$-C$_{20}$ alkynyl, —OC(O)cycloalkyl, —OC(O)aryl, —OC(O)NHC$_1$-C$_{20}$ alkyl, —OC(O)NHC$_2$-C$_{20}$ alkenyl, —OC(O)NHC$_2$-C$_{20}$ alkynyl, —OC(O)NHcycloalkyl, —OC(O)NHaryl, —OC(S)NHC$_1$-C$_{20}$ alkyl, —OC(S)NHC$_2$-C$_{20}$ alkenyl, —OC(S)NHC$_2$-C$_{20}$ alkynyl, —OC(S)NHcycloalkyl, or —OC(S)NHaryl, or $R^{21}$ and $R^{22}$ taken together form a carbonyl group;

$R^{23}$ is hydrogen, —OH, —OC$_1$-C$_{20}$ alkyl, —OC$_2$-C$_{20}$ alkenyl, —OC$_2$-C$_{20}$ alkynyl, —Ocycloalkyl, —OC(O)C$_1$-C$_{20}$ alkyl, —OC(O)C$_2$-C$_{20}$ alkenyl, —OC(O)C$_2$-C$_{20}$ alkynyl, —OC(O)cycloalkyl, —OC(O)aryl, —OC(O)NHC$_1$-C$_{20}$ alkyl, —OC(O)NHC$_2$-C$_{20}$ alkenyl, —OC(O)NHC$_2$-C$_{20}$ alkynyl, —OC(O)NHcycloalkyl, —OC(O)NHaryl, —OC(S)NHC$_1$-C$_{20}$ alkyl, —OC(S)NHC$_2$-C$_{20}$ alkenyl, —OC(S)NHC$_2$-C$_{20}$ alkynyl, —OC(S)NHcycloalkyl, or —OC(S)NHaryl;

$R^{24}$ is hydrogen, —OH, —OC$_1$-C$_{20}$ alkyl, —OC$_2$-C$_{20}$ alkenyl, —OC$_2$-C$_{20}$ alkynyl, —Ocycloalkyl, —OC(O)C$_1$-C$_{20}$ alkyl, —OC(O)C$_2$-C$_{20}$ alkenyl, —OC(O)C$_2$-C$_{20}$ alkynyl, —OC(O)cycloalkyl, —OC(O)aryl, —OC(O)NHC$_1$-C$_{20}$ alkyl, —OC(O)NHC$_2$-C$_{20}$ alkenyl, —OC(O)NHC$_2$-C$_{20}$ alkynyl, —OC(O)NHcycloalkyl, —OC(O)NHaryl, —OC(S)NHC$_1$-C$_{20}$ alkyl, —OC(S)NHC$_2$-C$_{20}$ alkenyl, —OC(S)NHC$_2$-C$_{20}$ alkynyl, —OC(S)NHcycloalkyl, or —OC(S)NHaryl;

$R^{25}$ is hydrogen or —C$_1$-C$_{10}$ alkyl;

$R^{26}$ and $R^{27}$ are each independently hydrogen, —C$_1$-C$_{10}$ alkyl, —OH, or —OC$_1$-C$_{10}$ alkyl;

wherein each alkyl, alkenyl, alkynyl, cycloalkyl and aryl is optionally substituted with one or more optional substituents, wherein each optional substituent is independently —F, —Cl, —Br, —I, —CN, —CF$_3$, —CO$_2$R$^{28}$, —COR$^{28}$, —OR$^{28}$, —SR$^{28}$, —N(R$^{28}$)$_2$, —NO$_2$, —NR$^{28}$OR$^{28}$, —ON(R28)2, —SOR$^{28}$, —SO$_2$R$^{28}$, —SO$_3$R$^{28}$, —SON(R$^{28}$)$_2$, —SON(R$^{28}$)$_2$, —SO$_3$N(R$^{28}$)$_2$, —P(R$^{28}$)$_3$, —P(═O)(R$^{28}$)$_3$, —OSi(R$^{28}$)$_3$ or —OB(R$^{28}$)$_2$, and wherein $R^{28}$ is hydrogen, —C$_1$-C$_6$alkyl, —C$_2$-C$_6$alkenyl, —C$_2$-C$_6$alkynyl, —C$_3$-C$_8$cycloalkyl, —C$_6$-C$_{14}$aryl, arylalkyl, —C$_1$-C$_6$haloalkyl, —C$_1$-C$_6$dihaloalkyl or —C$_1$-C$_6$trihaloalkyl;

and geometric isomers or stereoisomers thereof, or pharmaceutically, agriculturally or pesticidally acceptable salts thereof.

2. A compound according to claim 1, wherein the compound is a compound of formula (III):

(III)

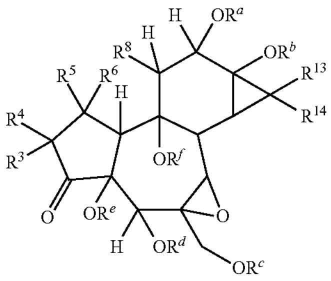

wherein:

$R^3$ is hydrogen, —$C_1$-$C_6$ alkyl or —$C_2$-$C_6$ alkenyl;

$R^4$ and $R^5$ are each independently hydrogen, —$C_1$-$C_6$ alkyl, —$C_2$-$C_6$ alkenyl, —OH, —O$C_1$-$C_6$ alkyl, —O$C_2$-$C_6$ alkenyl, —OC(O)$C_1$-$C_6$ alkyl, —OC(O)$C_2$-$C_6$ alkenyl, —OC(O)aryl, F, Cl, Br or I, or $R^4$ and $R^5$ taken together form a double bond or are —O—;

$R^6$ is hydrogen, —$C_1$-$C_6$ alkyl or —$C_2$-$C_6$ alkenyl;

$R^8$ is hydrogen, —$C_1$-$C_6$ alkyl or —$C_2$-$C_6$ alkenyl;

$R^{13}$ and $R^{14}$ are each independently hydrogen or —$C_1$-$C_6$ alkyl;

$R^a$ is hydrogen, —$C_1$-$C_{20}$ alkyl, —$C_2$-$C_{20}$ alkenyl, —$C_2$-$C_{20}$ alkynyl, —C(O)$C_2$-$C_{20}$ alkyl, —C(O)$C_2$-$C_{20}$ alkenyl, —OC(O)$C_2$-$C_{20}$ alkynyl, —C(O)cycloalkyl, —C(O)aryl, —C(O)NH$C_1$-$C_{20}$ alkyl, —C(O)NH$C_2$-$C_{20}$ alkenyl, —C(O)NH$C_2$-$C_{20}$ alkynyl, —C(O)NHcycloalkyl, —C(O)NHaryl, —C(S)NH$C_1$-$C_{20}$ alkyl, —C(S)NH$C_2$-$C_{20}$ alkenyl, —C(S)NH$C_2$-$C_{20}$ alkynyl, —C(S)NHcycloalkyl, or —C(S)NHaryl;

$R^b$, $R^C$, $R^d$, $R^e$ and $R^f$ are each independently hydrogen, —$C_1$-$C_{20}$ alkyl, —$C_2$-$C_{20}$ alkenyl, —$C_2$-$C_{20}$ alkynyl, —C(O)$C_1$-$C_{20}$ alkyl, —C(O)$C_2$-$C_{20}$ alkenyl, —OC(O)$C_2$-$C_{20}$ alkynyl, —C(O)cycloalkyl, —C(O)aryl, —C(O)NH$C_1$-$C_{20}$ alkyl, —C(O)NH$C_2$-$C_{20}$ alkenyl, —C(O)NH$C_2$-$C_{20}$ alkynyl, —C(O)NHcycloalkyl, —C(O)NHaryl, —C(S)NH$C_1$-$C_{20}$ alkyl, —C(S)NH$C_2$-$C_{20}$ alkenyl, —C(S)NH$C_2$-$C_{20}$ alkynyl, —C(S)NHcycloalkyl, or —C(S)NHaryl;

wherein each alkyl, alkenyl and aryl group is optionally substituted with one or more optional substituents, wherein each optional substituent is as defined in claim 1;

or geometric isomers or stereoisomers, or pharmaceutically, agriculturally or pesticidally acceptable salts thereof.

3. A compound according to claim 1, wherein the compound is a compound of formula (IV):

(IV)

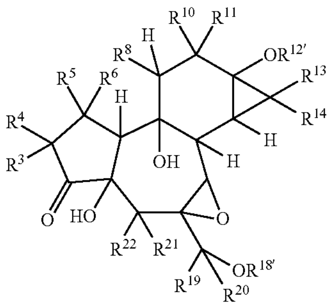

wherein:

$R^3$ is hydrogen, —$C_1$-$C_6$ alkyl or —$C_2$-$C_6$ alkenyl;

$R^4$ and $R^5$ are each independently hydrogen, —$C_1$-$C_6$ alkyl, —$C_2$-$C_6$ alkenyl, —OH, —O$C_1$-$C_6$ alkyl, —O$C_2$-$C_6$ alkenyl, —OC(O)$C_1$-$C_6$ alkyl, —OC(O)$C_2$-$C_6$ alkenyl, —OC(O)aryl, —OC(O)heterocyclyl, —OC(O)heteroaryl, F, Cl, Br or I, or $R^4$ and $R^5$ taken together form a double bond or are —O—;

$R^6$ is hydrogen, —$C_1$-$C_6$ alkyl or —$C_2$-$C_6$ alkenyl;

$R^8$ is hydrogen, —$C_1$-$C_6$ alkyl or —$C_2$-$C_6$ alkenyl;

$R^{10}$ is hydrogen;

$R^{11}$ is hydroxy, —O$C_1$-$C_{20}$ alkyl, —O$C_2$-$C_{20}$ alkenyl, —OC(O)$C_2$-$C_{20}$ alkyl, —OC(O)$C_2$-$C_{20}$ alkenyl or —OC(O)aryl, or $R^{10}$ and $R^{11}$ taken together form a carbonyl group;

$R^{12'}$ is hydrogen, —$C_1$-$C_{20}$ alkyl, —$C_2$-$C_{20}$ alkenyl, —C(O)$C_1$-$C_{20}$ alkyl, —C(O)$C_2$-$C_{20}$ alkenyl or —C(O)aryl;

$R^{13}$ and $R^{14}$ are each independently hydrogen or —$C_1$-$C_6$ alkyl;

$R^{18'}$ is hydrogen, —$C_1$-$C_6$ alkyl, —$C_2$-$C_6$ alkenyl, —C(O)$C_1$-$C_6$ alkyl, —C(O)$C_2$-$C_6$ alkenyl or —C(O)aryl;

$R^{19}$ and $R^{20}$ are each independently hydrogen, —OH, —O$C_1$-$C_6$ alkyl, or —O$C_2$-$C_6$ alkenyl, or $R^{19}$ and $R^{20}$ taken together form a carbonyl group;

$R^{21}$ is hydrogen;

$R^{22}$ is hydroxy, —O$C_1$-$C_6$ alkyl, —O$C_2$-$C_6$ alkenyl, —OC(O)$C_1$-$C_6$ alkyl, —OC(O)$C_2$-$C_6$ alkenyl, or —OC(O)aryl, or $R^{21}$ and $R^{22}$ taken together form a carbonyl group;

wherein each alkyl, alkenyl and aryl is optionally substituted with one or more optional substituents, wherein each optional substituent is as defined in claim 1;

and geometric isomers or stereoisomers thereof, or pharmaceutically, agriculturally or pesticidally acceptable salts thereof.

4. A compound according to claim 1 wherein $R^1$ and $R^2$ are each independently hydrogen, hydroxy, —O$C_1$-$C_6$ alkyl, —O$C_2$-$C_6$ alkenyl, —OC(O)$C_1$-$C_6$ alkyl or —OC(O)$C_2$-$C_6$ alkenyl, or $R^1$ and $R^2$ taken together form a carbonyl group.

5. A compound according to claim 1 wherein $R^4$ and $R^5$ form a double bond or $R^4$ and $R^5$ are hydrogen or together are —O—.

6. A compound according to claim 1 wherein $R^8$ is hydrogen or —$C_1$-$C_3$ alkyl.

7. A compound according to claim 1 wherein $R^{11}$ is hydroxy, —$C_1$-$C_{20}$ alkyloxy, —$C_2$-$C_{20}$ alkenyloxy, —OC(O)$C_2$-$C_{20}$ alkyl or —OC(O)$C_2$-$C_{20}$ alkenyl, and $R^{12}$ is hydroxy, —$C_1$-$C_{20}$ alkyloxy, —$C_2$-$C_{20}$ alkenyloxy, —OC(O)$C_1$-$C_{20}$ alkyl or —OC(O)$C_2$-$C_{20}$ alkenyl.

8. A compound according to claim 1 wherein $R^{13}$ and $R^{14}$ are each independently hydrogen or —$C_1$-$C_3$ alkyl.

9. A compound according to claim 1 wherein $R^{19}$ and $R^{20}$ are each independently hydrogen, hydroxy, —O$C_1$-$C_3$ alkyl, or —O$C_2$-$C_3$ alkenyl, or $R^{19}$ and $R^{20}$ taken together form a carbonyl group and $R^{18}$ is hydroxy, —O$C_1$-$C_6$ alkyl, —O$C_2$-$C_6$ alkenyl, —OC(O)$C_1$-$C_6$ alkyl or —OC(O)$C_2$-$C_6$ alkenyl.

10. A compound according to claim 1 wherein $R^{22}$ is hydroxy, —O$C_1$-$C_6$ alkyl, —O$C_2$-$C_6$ alkenyl, —OC(O)$C_1$-$C_6$ alkyl or —OC(O)$C_2$-$C_6$ alkenyl.

11. A compound according to claim 1 wherein $R^{23}$ and $R^{24}$ are each hydroxy.

12. A compound according to claim 1 which is:

(12-tigloyl-13-(2-methylbutanoyl)-6,7-epoxy-4,5,9,12,13,20-hexahydroxy-1-tigliaen-3-one);

(12,13-di-(2-methylbutanoyl)-6,7-epoxy-4,5,9,12,13,20-hexahydroxy-tigliaen-3-one);

12-(dodeca-2,4,6-trienoyl)-13-(2-methylbutanoyl)-6,7-epoxy-4,5,9,12,13,20-hexahydroxy-1-tigliaen-3-one;

12-(deca-2,4-dienoyl)-6,7-epoxy-4,5,9,12,13,20-hexahydroxy-1-tigliaen-3-one;

12,13-di-(2-methylbutanoyl)-1,2-2H-1,2,6,7-diepoxy-6-carboxy-4,5,9,12,13-pentahydroxy-tigliaen-3-one; and 12,13-di-(2-methylbutanoyl)-5,20-di-acetoyl-4,5,9,12,13,20-hexahydroxy-tigliaen-3-one.

13. A pharmaceutical or pesticidal composition comprising a compound of formula (II):

(II)

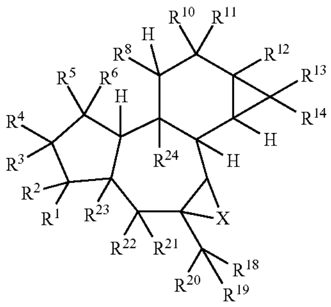

wherein:

X is —O—;

$R^1$ and $R^2$ are each independently hydrogen, —OH, —$OC_1$-$C_{10}$ alkyl, —$OC_2$-$C_{10}$ alkenyl, —$OC_2$-$C_{10}$ alkynyl, —Ocycloalkyl, —OC(O)$C_1$-$C_{10}$ alkyl, —OC(O)$C_2$-$C_{10}$ alkenyl, —OC(O)$C_2$-$C_{10}$ alkynyl, —OC(O)cycloalkyl, —OC(O)NH$C_1$-$C_{10}$ alkyl, —OC(O)NH$C_2$-$C_{10}$ alkenyl, —OC(O)NH$C_2$-$C_{10}$ alkynyl, —OC(O)NHcycloalkyl, —OC(O)NHaryl, —OC(S)NH$C_1$-$C_{10}$ alkyl, —OC(S)NH$C_2$-$C_{10}$ alkenyl, —OC(S)NH$C_2$-$C_{10}$ alkynyl, —OC(S)NHcycloalkyl or —OC(S)NHaryl, or $R^1$ and $R^2$ taken together are =O, =S, =NH or =N($C_1$-$C_6$ alkyl);

$R^3$ is hydrogen, —$C_1$-$C_{10}$ alkyl, —$C_2$-$C_{10}$ alkenyl or —$C_2$-$C_{10}$ alkynyl;

$R^4$ and $R^5$ are each independently hydrogen, —$C_1$-$C_{10}$ alkyl, —$C_2$-$C_{10}$ alkenyl, —$C_2$-$C_{10}$ alkynyl, —OH, —$OC_1$-$C_{10}$ alkyl, —$OC_2$-$C_{10}$ alkenyl, —$OC_2$-$C_{10}$ alkynyl, —Ocycloalkyl, —OC(O)$C_1$-$C_{10}$ alkyl, —OC(O)$C_2$-$C_{10}$ alkenyl, —OC(O)$C_2$-$C_{10}$ alkynyl, —OC(O)cycloalkyl, —OC(O)aryl, —OC(O)NH$C_1$-$C_{10}$ alkyl, —OC(O)NH$C_2$-$C_{10}$ alkenyl, —OC(O)NH$C_2$-$C_{10}$ alkynyl, —OC(O)NHcycloalkyl, —OC(O)NHaryl, —OC(S)NH$C_1$-$C_{10}$ alkyl, —OC(S)NH$C_2$-$C_{10}$ alkenyl, —OC(S)NH$C_2$-$C_{10}$ alkynyl, —OC(S)NHcycloalkyl, —OC(S)NHaryl, F, Cl, Br, I, —CN, —$NO_2$ or N($R^{25}$)$_2$, or $R^4$ and $R^5$ taken together form a double bond or are —O—, —S—, —$NR^{25}$— or —$CR^{26}R^{27}$—;

$R^6$ is hydrogen, —$C_1$-$C_{10}$ alkyl, —$C_2$-$C_{10}$ alkenyl or —$C_2$-$C_{10}$ alkynyl;

$R^8$ is hydrogen, —$C_1$-$C_{10}$ alkyl, —$C_2$-$C_{10}$ alkenyl or —$C_2$-$C_{10}$ alkynyl;

$R^{10}$ is hydrogen, —$C_1$-$C_{10}$ alkyl, —$C_2$-$C_{10}$ alkenyl or —$C_2$-$C_{10}$ alkynyl;

$R^{11}$ is —OH, —$OC_1$-$C_{20}$ alkyl, —$OC_2$-$C_{20}$ alkenyl, —$OC_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl or —OC(S)NHaryl, or $R^{10}$ and $R^{11}$ taken together form a carbonyl group (=O);

$R^{12}$ is —OH, —$OC_1$-$C_{20}$ alkyl, —$OC_2$-$C_{20}$ alkenyl, —$OC_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl or —OC(S)NHaryl;

$R^{13}$ and $R^{14}$ are each independently hydrogen or —$C_1$-$C_{10}$ alkyl;

$R^{18}$ is $C_1$-$C_{20}$ alkyl, —$C_2$-$C_{20}$ alkenyl, —$C_2$-$C_{20}$ alkynyl, —OH, —$OC_1$-$C_{20}$ alkyl, —$OC_2$-$C_{20}$ alkenyl, —$OC_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —NH$C_1$-$C_{20}$ alkyl, —NH$C_2$-$C_{20}$ alkenyl, —NH$C_2$-$C_{20}$ alkynyl, —NHcycloalkyl, —NHaryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl or —OC(S)NHaryl;

$R^{19}$ and $R^{20}$ are each independently hydrogen, —$C_1$-$C_6$ alkyl, —$C_2$-$C_6$ alkenyl, —$C_2$-$C_{20}$ alkynyl, —OH, —$OC_1$-$C_6$ alkyl, —$OC_2$-$C_6$ alkenyl, —$OC_2$-$C_6$ alkynyl, —Ocycloalkyl, —OC(O)$C_1$-$C_6$ alkyl, —OC(O)$C_2$-$C_6$ alkenyl, —OC(O)$C_2$-$C_6$ alkynyl, —OC(O)cycloalkyl or —OC(O)aryl, or $R^{19}$ and $R^{20}$ taken together form a carbonyl or thiocarbonyl group;

$R^{21}$ is hydrogen, —$C_1$-$C_{10}$ alkyl, —$C_2$-$C_{10}$ alkenyl or —$C_2$-$C_{10}$ alkynyl;

$R^{22}$ is —OH, —$OC_1$-$C_{20}$ alkyl, —$OC_2$-$C_{20}$ alkenyl, —$OC_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl or —OC(S)NHaryl, or $R^{21}$ and $R^{22}$ taken together form a carbonyl group;

$R^{23}$ is hydrogen, —OH, —$OC_1$-$C_{20}$ alkyl, —$OC_2$-$C_{20}$ alkenyl, —$OC_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(S)NH$C_1$-$C_{20}$ alkyl, —OC(S)NH$C_2$-$C_{20}$ alkenyl, —OC(S)NH$C_2$-$C_{20}$ alkynyl, —OC(S)NHcycloalkyl or —OC(S)NHaryl;

$R^{24}$ is hydrogen, —OH, —$OC_1$-$C_{20}$ alkyl, —$OC_2$-$C_{20}$ alkenyl, —$OC_2$-$C_{20}$ alkynyl, —Ocycloalkyl, —OC(O)$C_1$-$C_{20}$ alkyl, —OC(O)$C_2$-$C_{20}$ alkenyl, —OC(O)$C_2$-$C_{20}$ alkynyl, —OC(O)cycloalkyl, —OC(O)aryl, —OC(O)NH$C_1$-$C_{20}$ alkyl, —OC(O)NH$C_2$-$C_{20}$ alkenyl, —OC(O)NH$C_2$-$C_{20}$ alkynyl, —OC(O)NHcycloalkyl, —OC(O)NHaryl, —OC(S)NHC$_1$-C$_{20}$ alkyl, —OC(S)NHC$_2$-C$_{20}$ alkenyl, —OC(S)NHC$_2$-C$_{20}$ alkynyl, —OC(S)NHcycloalkyl or —OC(S)NHaryl;

$R^{25}$ is hydrogen or —C$_1$-C$_{10}$ alkyl;

$R^{26}$ and $R^{27}$ are each independently hydrogen, —C$_1$-C$_{10}$ alkyl, —OH or —OC$_1$-C$_{10}$ alkyl;

wherein each alkyl, alkenyl, alkynyl, cycloalkyl and aryl is optionally substituted with one or more optional substituents, wherein each optional substituent is independently —F, —Cl, —Br, —I, —CN, —CF$_3$, —CO$_2$R$^{28}$, —COR$^{28}$, —OR$^{28}$, —SR$^{28}$, —N(R$^{28}$)$_2$, —NO$_2$, —NR$^{28}$OR$^{28}$, —ON(R$^{28}$)$_2$, —SOR$^{28}$, —SO$_2$R$^{28}$, —SO$_3$R$^{28}$, —SON(R$^{28}$)$_2$, —SON(R$^{28}$)$_2$, —SO$_3$N(R$^{28}$)$_2$, —P(R$^{28}$)$_3$, —P(═O)(R$^{28}$)$_3$, —OSi(R$^{28}$)$_3$ or —OB(R$^{28}$)$_2$, and wherein $R^{28}$ is hydrogen, —C$_1$-C$_6$alkyl, —C$_2$-C$_6$alkenyl, —C$_2$-C$_6$alkynyl, —C$_3$-C$_8$cycloalkyl, —C$_6$-C$_{14}$aryl, arylalkyl, —C$_1$-C$_6$haloalkyl, —C$_1$-C$_6$dihaloalkyl or —C$_1$-C$_6$trihaloalkyl;

and geometric isomers or stereoisomers thereof, or pharmaceutically, agriculturally or pesticidally acceptable salts thereof;

and a pharmaceutically, agriculturally or pesticidally acceptable carrier.

* * * * *

UNITED STATES PATENT AND TRADEMARK OFFICE

CERTIFICATE OF CORRECTION

PATENT NO. : 8,598,229 B2
APPLICATION NO. : 12/158461
DATED : December 3, 2013
INVENTOR(S) : Paul Warren Reddell et al.

It is certified that error appears in the above-identified patent and that said Letters Patent is hereby corrected as shown below:

Title page

Item (56):
"Hanipson et al., "PEP005, a selective small-molecule activator of protein kinase C. has potent antileukemic activity mediated via the delta Isoform of PKC," Blood 106(4):1362-1368, 2005." should read, --Hampson et al., "PEP005, a selective small-molecule activator of protein kinase C, has potent antileukemic activity mediated via the delta isoform of PKC," Blood 106(4):1362-1368, 2005.--.

In the Claims

Column 47, Line 36, Claim 2:
"$R^b$, $R^C$, $R^d$, $R^e$, and R' are each independently hydrogen," should read, --$R^b$, $R^c$, $R^d$, $R^e$, and $R^f$ are each independently hydrogen,--.

Signed and Sealed this
Eighteenth Day of August, 2015

Michelle K. Lee
*Director of the United States Patent and Trademark Office*